United States Patent [19]

Mickel et al.

[11] Patent Number: 5,190,934

[45] Date of Patent: Mar. 2, 1993

[54] P-SUBSITUTED PROPANE-PHOSPHINIC ACID COMPOUNDS

[75] Inventors: Stuart J. Mickel, Lausen; Georg von Sprecher, Oberwil, both of Switzerland

[73] Assignee: Ciba-Geigy Corporation, New York, N.Y.

[21] Appl. No.: 845,869

[22] Filed: Mar. 3, 1992

Related U.S. Application Data

[63] Continuation of Ser. No. 759,210, Sep. 13, 1991, abandoned, which is a continuation of Ser. No. 528,673, May 24, 1990, abandoned.

[30] Foreign Application Priority Data

Jun. 3, 1989 [GB] United Kingdom ............... 8912814

[51] Int. Cl.$^5$ ..................... C07F 9/30; A61K 31/44; A61K 31/66; A61K 31/185
[52] U.S. Cl. ..................... 514/114; 514/89; 514/91; 546/22; 548/413; 562/11
[58] Field of Search ............... 514/114, 89, 91; 546/22; 548/413; 562/11

[56] References Cited

U.S. PATENT DOCUMENTS

| | | | |
|---|---|---|---|
| 2,535,175 | 5/1949 | Tawney | 260/461 |
| 3,184,496 | 5/1965 | Baranauckas | 260/461 |
| 3,374,288 | 3/1968 | Lange | 260/857 |
| 3,385,822 | 3/1968 | Brown | 260/465 |
| 3,493,639 | 2/1970 | Tavs | 562/11 |
| 3,637,763 | 1/1972 | Firestone | 260/348 |
| 3,812,221 | 5/1974 | Braden et al. | 562/11 |
| 3,970,586 | 7/1976 | Schliebs | 252/355 |
| 4,064,163 | 12/1977 | Drach | 260/502.4 R |
| 4,322,375 | 3/1982 | Maier | 260/951 |
| 4,390,690 | 6/1983 | DiGiacamo | 528/395 |
| 4,399,287 | 8/1983 | Baillie | 548/119 |
| 4,466,913 | 8/1984 | Tsuruoka | 260/112.5 R |
| 4,536,355 | 8/1985 | Lee | 260/944 |
| 4,656,298 | 4/1987 | Dingwall et al. | 562/11 |
| 4,740,322 | 4/1988 | Thottathil | 260/502.4 R |
| 4,772,738 | 9/1988 | Dingwall | 558/175 |
| 4,908,465 | 3/1990 | Dingwall | 558/175 |
| 5,004,826 | 4/1991 | Dingwall | 558/169 |
| 5,013,863 | 5/1991 | Baylis | 562/11 |
| 5,051,524 | 9/1991 | Baylis | 558/145 |
| 5,064,819 | 11/1991 | Baylis et al. | 514/114 |

FOREIGN PATENT DOCUMENTS

| | | |
|---|---|---|
| 009348 | 4/1980 | European Pat. Off. . |
| 0068497 | 1/1983 | European Pat. Off. . |
| 0093081 | 11/1983 | European Pat. Off. . |
| 0181833 | 5/1986 | European Pat. Off. . |
| 0181833 | 5/1986 | European Pat. Off. . |
| 319482 | 12/1988 | European Pat. Off. . |
| 0319479 | 6/1989 | European Pat. Off. . |
| 319479 | 6/1989 | European Pat. Off. ............ 562/11 |
| 319482 | 6/1989 | European Pat. Off. ............ 562/11 |
| 0356128 | 2/1990 | European Pat. Off. . |
| 0356128 | 2/1990 | European Pat. Off. . |
| 1151592 | 6/1989 | Japan . |
| 166693 | 12/1964 | U.S.S.R. . |
| 463675 | 3/1975 | U.S.S.R. . |
| 1174439 | 6/1984 | U.S.S.R. . |
| 1525262 | 8/1974 | United Kingdom . |
| 1351503 | 7/1990 | United Kingdom . |

OTHER PUBLICATIONS

Neurology 41 (Supp. 1) 151, Abs 131S (1991).
Annual Meeting of the Society for Neuroscience New Orleans Nov. 10–15, 1991.
Aust. J. Chem 33, (1980), pp. 287–294.
Br. J. Pharm 101, 949 (1990).
Chem Abs 57, 5946 (1962).
Chem Abs 97, 92585v (1982).
J. Med Chem 27, 654 (1984).
J. Pharma and Experimental Ther 235(1) (1985).
Phosporous and Sulfur 18, 353–356 (1983).

*Primary Examiner*—Joseph E. Evans
*Attorney, Agent, or Firm*—Irving M. Fishman; Karen G. Kaiser

[57] ABSTRACT

Compounds of the formula I

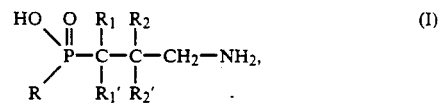

wherein either $R_1$ is halogen, $R_1'$ is halogen or hydrogen and $R_2$ and $R_2'$ denote hydrogen or $R_1$ and $R_1'$ represent hydrogen, $R_2$ is an aliphatic or aromatic radical and $R_2'$ is hydroxy or $R_2$ and $R_2'$ together represent oxo, and wherein R denotes an aliphatic, cycloaliphatic, cycloaliphatic-aliphatic or araliphatic radical having 2 or more carbon atoms or, if $R_1$ and $R_1'$ denote hydrogen, $R_2$ represents an aromatic radical and $R_2'$ is hydroxy, R represents methyl, and their salts are useful as nootropics, antidepressants and/or anxiolytics. The can be manufacture by replacing any group $R_5$ by hydrogen and/or converting any group $Z_0$ into amino in a compound of formula II

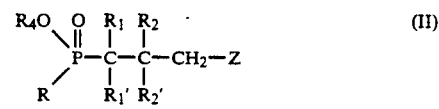

in which R, $R_1$, $R_1'$, $R_2$ and $R_2'$ have their previous significances, Z represents a protected or latent amino group $Z_0$ and $R_4$ denotes hydrogen or a hyddroxy-protective group $R_5$, and wherein amino as a constituent of R and/or hydroxy $R_2'$ or oxo $R_2+R_2'$ may be present in a temporarily protected form.

22 Claims, No Drawings

P-SUBSITUTED PROPANE-PHOSPHINIC ACID COMPOUNDS

This application is a continuation of application Ser. No. 07/759,210 filed on Sep. 13, 1991, now abandoned, which in turn is a continuation of application Ser. No. 07/528,673 filed on May 24, 1990, now abandoned.

The invention relates to compounds of the formula I

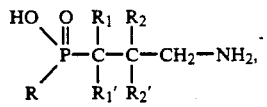

wherein either $R_1$ is halogen, $R_1'$ is halogen or hydrogen and $R_2$ and $R_2'$ denote hydrogen or $R_1$ and $R_1'$ represent hydrogen, $R_2$ is an aliphatic or aromatic radical and $R_2'$ is hydroxy or $R_2$ and $R_2'$ together represent oxo, and wherein R denotes an aliphatic, cycloaliphatic, cycloaliphatic-aliphatic or araliphatic radical having 2 or more carbon atoms or, if $R_1$ and $R_1'$ denote hydrogen, $R_2$ represents an aromatic radical and $R_2'$ is hydroxy, R represents methyl, and to their salts, to a process for the manufacture of compounds of the formula I, to pharmaceutical compositions containing the same and to their use as a medicament or for the manufacture thereof.

Aliphatic radicals R are, for example, alkyl groups that may be interrupted by one or two mutually spaced atoms selected from oxygen and sulphur and/or substituted by halogen, hydroxy, oxo and/or optionally acylated amino, such as alkyl, alkyl mono-, di- or polysubstituted by halogen and/or hydroxy, alkyl substituted by oxo, alkyl substituted by optionally acylated amino or by hydroxy and optionally acylated amino, alkyl being interrupted by one or two mutually spaced atoms selected from oxygen and sulphur or alkyl being interrupted by one or two mutually spaced atoms selected from oxygen and sulphur and substituted by halogen and/or hydroxy, alkenyl groups that may be mono-, di-or polysubstituted by halogen and/or hydroxy, such as lower alkenyl or lower alkenyl substituted by halogen and/or hydroxy, or alkynyl groups, such as lower alkynyl.

Cycloaliphatic radicals R are, for example, cycloalkyl groups that may be interrupted by one or two mutually spaced atoms selected from oxygen and sulphur and/or substituted by hydroxy, such as cycloalkyl, cycloalkyl being interrupted by one or two mutually spaced atoms selected from oxygen and sulphur or cycloalkyl substituted by hydroxy.

Cycloaliphatic-aliphatic radicals R are, for example, cycloalkyl-lower alkyl groups that may be interrupted by one or two mutually spaced atoms selected from oxygen and sulphur and/or substituted by hydroxy and/or lower alkylthio, such as cycloalkyl-lower alkyl, cycloalkyl-lower alkyl being interrupted by one or two mutually spaced atoms selected from oxygen and sulphur or cycloalkyl-lower alkyl substituted in the cycloalkyl moiety by hydroxy or lower alkylthio and/or in the alkylene moiety by hydroxy.

Araliphatic radicals R are, for example, phenyl-lower alkyl or naphthyl-lower alkyl radicals that may be substituted in the aryl ring by halogen, lower alkyl, lower alkoxy and/or trifluoromethyl and/or in the lower alkylene moiety by hydroxy, such as phenyl-lower alkyl, phenyl-(1-hydroxy)-lower alkyl, naphthyl-lower alkyl or phenyl-lower alkyl substituted in the phenyl moiety by halogen, lower alkyl, lower alkoxy and/or trifluoromethyl.

Aromatic radicals $R_2$ may be carbocyclic or heterocyclic aromatic radical, such as phenyl, naphthyl, or phenyl substituted by halogen, lower alkyl, lower alkoxy and/or trifluoromethyl or pyridyl.

In compounds of formula I the group R is bonded to the P-atom via a carbon atom.

Optionally acylated amino is, for example, amino, lower alkanoylamino or phthalimido.

Alkyl, alkenyl and alkynyl R may contain up to and including 14, preferably 12 carbon atoms and are represented by lower alkyl, lower alkenyl and lower alkynyl. Alkyl R may also be a $C_8$–$C_{14}$-, e.g. a $C_8$–$C_{12}$-alkyl, such as an octyl, nonyl, decyl, undecyl or dodecyl group, e.g. a decyl or dodecyl group.

Alkyl or alkenyl mono-, di- or polysubstituted by halogen and/or hydroxy is represented by mono- or dihydroxy-lower alkyl, hydroxy-lower alkenyl, mono-, di- or polyhalogeno-lower alkyl, mono-, di- or polyhalogeno-lower alkenyl, mono-, di- or polyhalogeno-lower hydroxyalkyl and mono-, di- or polyhalogeno-lower hydroxyalkenyl.

Alkyl substituted by oxo is, for example oxo-lower alkyl.

Alkyl substituted by optionally acylated amino is, for example, amino-lower alkyl, N-lower alkanoylamino-lower alkyl or phthalimido-lower alkyl.

Alkyl substituted by optionally acylated amino and by hydroxy is, for example, amino-lower hydroxyalkyl, N-lower alkanoylamino-lower hydroxyalkyl or phthalimido-lower hydroxyalkyl.

Alkyl being interrupted by one or two atoms selected from oxygen and sulphur is represented by lower alkoxy-lower alkyl, lower alkylthio-lower alkyl, lower alkanesulphinyl-lower alkyl, lower alkanesulphonyl-lower alkyl, lower alkoxy-lower alkoxy-lower alkyl, di-lower alkoxy-lower alkyl, di-lower alkylthio-lower alkyl, and lower alkoxy-lower alkylthio-lower alkyl.

Alkyl being interrupted by one or two atoms selected from oxygen and sulphur and substituted by hydroxy and/or halogen is represented by lower alkoxy-(hydroxy)lower alkyl and lower alkoxy-(halogeno)lower alkyl.

Cycloalkyl is represented by $C_3$–$C_8$-cycloalkyl.

Cycloalkyl substituted by hydroxy is represented by 1-hydroxy-$C_3$–$C_8$-cycloalkyl.

Cycloalkyl and cycloalkyl in cycloalkyl-lower alkyl, in either case, being interrupted by one or two atoms selected from oxygen and sulphur is represented by oxa-$C_3$–$C_8$-cycloalkyl, thia-$C_3$–$C_8$-cycloalkyl, dioxa-$C_3$–$C_8$-cycloalkyl, dithia-$C_3$–$C_8$-cycloalkyl and oxathia-$C_3$–$C_8$-cycloalkyl.

Cycloalkyl-lower alkyl substituted in the cycloalkyl moiety by hydroxy and/or lower alkylthio and/or in the alkylene moiety by hydroxy is represented by lower alkylthiocycloalkyl-lower alkyl, cycloalkyl-(hydroxy)-lower alkyl and lower alkylthiocycloalkyl-(hydroxy)-lower alkyl.

The general definitions used herein have the following meaning within the scope of the present invention.

The term "lower" referred to above and hereinafter in connection with organic radicals or compounds respectively, if not defined explicitly otherwise, defines such with up to and including 7, preferably up to and including 4, carbon atoms.

Lower alkyl R is represented by $C_2$–$C_7$-alkyl, e.g. ethyl, propyl, isopropyl, butyl, isobutyl, sec.-butyl, tert.-butyl, (2-methyl)butyl, hexyl or heptyl. Lower alkyl other than R denotes, for example, $C_1$–$C_4$-alkyl, e.g. methyl, ethyl, propyl, isopropyl, butyl or tert.-butyl.

Lower alkenyl denotes, for example, $C_2$–$C_7$-alkenyl, preferably $C_3$–$C_5$-alkenyl, carrying the double bond in a higher than the $\alpha,\beta$-position, and is e.g. 2-propenyl (allyl), but-3-en-1-yl,(2-methyl)prop-2-en-1-yl (isobutenyl) or (5-methyl)but-2-en-1-yl, but may also carry the double bond in $\alpha,\beta$-position and may be, for example, vinyl, prop-1-enyl or but-1-enyl, or may be a $C_6$- or $C_7$-alkenyl, such as a hexenyl or heptenyl, group.

Lower alkynyl denotes, for example, $C_2$–$C_7$-alkynyl, preferably $C_3$–$C_5$-alkynyl, carrying the triple bond in a higher than the $\alpha,\beta$-position and is e.g. 2-propynyl (propargyl), but-3-yn-1-yl, but-2-yn-1-yl or pent-3-yn-1-yl.

$C_3$–$C_8$-Cycloalkyl preferably has 3 to 6 ring carbon atoms and thus is $C_3$–$C_6$-cycloalkyl, e.g. cyclopropyl, cyclobutyl, cyclopentyl or cyclohexyl.

$C_3$–$C_8$-Cycloalkyl-lower alkyl preferably has 3 to 6 ring and 1 to 4 chain carbon atoms and is, for example, $C_3$–$C_6$-cycloalkyl-$C_1$–$C_4$-alkyl, such as cyclopropylmethyl, cyclobutylmethyl or cyclohexylmethyl.

Mono- or dihydroxy-lower alkyl preferably carries one of the hydroxy groups in $\alpha$-position and is for example, $\alpha$-hydroxy-$C_2$–$C_7$-alkyl, such as $\alpha$-hydroxy-$C_2$–$C_4$-alkyl, e.g. 1-hydroxyethyl, 2-(2-hydroxy)propyl, 1-hydroxybutyl, 2-(2-hydroxy)butyl or 1-(1-hydroxy-2-methyl)propyl, or $\alpha, \beta$-dihydroxy-$C_2$–$C_7$-alkyl, such as 1,2-dihydroxy-prop-2-yl, but may also carry a single hydroxy group in a higher than the $\alpha$-position and denote, for example, $\beta$-, $\gamma$- or $\delta$-hydroxy -$C_2$–$C_7$-alkyl, e.g. 3-hydroxypropyl or 2-, 3- or 4-hydroxybutyl.

Hydroxy-lower alkenyl preferably carries the hydroxy group in $\alpha$-position and the double bond in a higher than the $\alpha,\beta$-position and is, for example, corresponding $\alpha$-hydroxy-$C_3$–$C_5$-alkenyl, e.g. 1-hydroxybut-2-enyl.

Mono-, di- or polyhalogeno-lower alkyl is for example, mono-, di-or trifluoro-$C_2$–$C_5$-alkyl, e.g. 3,3,3-trifluoropropyl, 4,4,4-trifluorobutyl, 1- or 2-fluorobutyl or 1,1-difluorobutyl.

Mono-, di- or polyhalogeno-lower alkenyl is, for example, mono-, di- or trifluoro-$C_3$–$C_5$-alkenyl, e.g. 2-fluorobut-2-enyl.

Mono-, di- or polyhalogeno-lower hydroxyalkyl and mono-, di- or polyhalogeno-lower hydroxyalkenyl preferably carries the hydroxy group in $\alpha$-position and the halogen atom(s) in a higher than the $\alpha$-position and is, for example, corresponding mono-, di- or trifluoro-$\alpha$-hydroxy-$C_2$–$C_7$-alkyl or mono- di- or trifluoro-$C_3$–$C_7$-alkenyl, e.g. 2-fluoro-1-hydroxybutyl, 2-fluoro-1-hydroxy-but-2-en-1-yl or 4,4,4-trifluoro-1-hydroxybutyl.

Lower alkoxy-lower alkyl preferably has up to 10 carbon atoms and is, for example, $C_1$–$C_4$-alkoxy-$C_1$–$C_4$-alkyl, such as $C_1$–$C_3$-alkoxy-$C_1$–$C_3$-alkyl, e.g. methoxymethyl, ethoxymethyl, 2-methoxyethyl, 2-ethoxyethyl, 3-methoxypropyl or 1- or 2-methoxybutyl.

Lower alkoxy is, for example, $C_1$–$C_4$-alkoxy, e.g. methoxy, ethoxy, isopropyloxy, propyloxy, butyloxy, sec.-butyloxy or tert.-butyloxy.

Lower alkoxy-lower alkoxy-lower alkyl is, for example, $C_1$–$C_4$-alkoxy-$C_2$–$C_4$-alkoxy-$C_1$–$C_4$-alkyl, e.g. 2-methoxyethoxymethyl.

Lower alkylthio-lower alkyl preferably has up to 10 carbon atoms and is, for example, $C_1$–$C_4$-alkylthio-$C_1$–$C_4$-alkyl, such as $C_1$–$C_3$-alkylthio-$C_1$–$C_3$-alkyl, e.g. methylthiomethyl, ethylthiomethyl, 2-methylthioethyl, 2-ethylthioethyl or 3-methylthiopropyl.

Lower alkansulphinyl- and lower alkanesulphonyl-lower alkyl preferably has up to 10 carbon atoms and is, for example, $C_1$–$C_4$-alkanesulfinyl- or $C_1$–$C_4$-alkanesulfonyl-$C_1$–$C_4$-alkyl, e.g. ethanesulphinylmethyl or ethanesulphonylmethyl.

Di-lower alkoxy-lower alkyl preferably has up to 15 carbon atoms totally and is, for example, di-$C_1$–$C_4$-alkoxy-$C_1$–$C_3$-alkyl, such as di-$C_1$–$C_3$-alkoxy-$C_1$–$C_3$-alkyl, e.g. dimethoxymethyl, diethoxymethyl, dipropyloxymethyl, 1,1- or 2,2-diethoxyethyl, diisopropyloxymethyl, di-n-butyloxymethyl or 3,3-dimethoxypropyl.

Di-lower alkylthio-lower alkyl preferably has up to 15 carbon atoms totally and is, for example, di-$C_1$–$C_4$-alkylthio-$C_1$–$C_4$-alkyl, such as di-$C_1$–$C_3$-alkylthio-$C_1$–$C_3$-alkyl, e.g. dimethylthiomethyl, diethylthiomethyl or 1,1- or 2,2-dimethylthioethyl.

Lower alkoxy-(hydroxy)lower alkyl is, for example $C_1$–$C_4$-alkoxy-$C_1$–$C_7$-(hydroxy)alkyl e.g. 2-(2-hydroxy-3-methoxy)propyl.

Lower alkoxy-(halogeno)lower alkyl is, for example $C_1$–$C_4$-alkoxy-$C_1$–$C_7$-(halogeno)alkyl e.g. 1-(2-fluoro-1-methoxy)butyl.

Oxo-lower alkyl carries the oxo group preferably in a position higher than the $\alpha$-position and is, for example, oxo-$C_2$–$C_7$alkyl, especially oxo-$C_3$–$C_6$alkyl, such as 2-oxopropyl, 2- or 3-oxobutyl or 3-oxopentyl.

Amino-lower alkyl is, for example, amino-$C_2$–$C_7$alkyl, especially amino-$C_3$–$C_6$alkyl, such as 3-aminopropyl or 3- or 4-aminobutyl. Similarly, N-lower alkanoylamino-lower alkyl and phthalimido-lower alkyl is, for example, N-$C_2$–$C_7$alkanoylamino- or phthalimido-$C_2$–$C_7$alkyl, especially -$C_3$–$C_6$alkyl, such as 3-acetamidopropyl, 3- or 4-acetamido butyl, 3-phthalimidopropyl or 3- or 4-phthalimidobutyl.

Amino-lower hydroxyalkyl is, for example, amino-$C_3$–$C_7$(hydroxy)alkyl, such as 3-amino-2-hydroxy-propyl or 4-amino-2-hydroxybutyl. Similarly, N-lower alkanoylamino-lower hydroxyalkyl and phthalimido-lower hydroxyalkyl is, for example, N-$C_2$–$C_7$alkanoylamino- or phthalimido-$C_2$–$C_7$alkyl, especially -$C_3$–$C_7$alkyl, such as 3-acetamido- or 3-phthalimido-2-hydroxy-propyl or 4-phthalimido-2-hydroxybutyl.

Hydroxy-$C_3$–$C_8$-cycloalkyl is, for example, 1-hydroxy-$C_3$–$C_6$-cycloalkyl, e.g. 1-hydroxycyclobutyl.

Oxa- or thia-$C_3$–$C_8$-cycloalkyl preferably has 2 to 6 ring carbon atoms is, for example, 2-oxacyclopropyl (oxiranyl), 2- or 3-oxacyclobutyl (oxetanyl), 2- or 3-thiacyclobutyl (thietanyl), 2- or 3-oxacylcopentyl (tetrahydrofuranyl), 2- or 3-thiacyclopentyl (thiolanyl) or 2-oxacyclohexyl (tetrahydropyranyl).

Dioxa-$C_3$–$C_8$-cycloalkyl preferably has 3 to 5 ring carbon atoms and carries those two oxygen atoms in 1,3-position to each other, and represents e.g. 1,3-dioxolan-2-yl or 1,3-dioxan-2-yl.

Dithia-$C_3$–$C_8$-cycloalkyl preferably has 3 to 5 ring carbon atoms and carries those two sulphur atoms in 1,3-position to each other and represents e.g. 1,3-dithiolan-2-yl or 1,3-dithioxan-2-yl. Oxathio-$C_3$–$C_8$-cycloalkyl is, for example 1,3-oxathiolan-2-yl or 1,3-oxathioxan-2-yl.

$C_3$-$C_8$-Cycloalkyl-(hydroxy)lower alkyl preferably has 3 to 6 ring and 1 to 4 chain carbon atoms and is, for example, cyclo-$C_3$-$C_6$-alkyl-$C_1$-$C_4$-alkyl, e.g. 1-cyclopropyl-1-hydroxymethyl or 1-hydroxy-1-cyclobutylmethyl. Lower alkylthiocycloalkyl-(hydroxy) lower alkyl is, for example, 1-hydroxy-1-(2-methylthiocyclopropyl).

Halogen, $R_1$, $R_1'$ and/or as a substituent of aromatic radicals $R_2$, is preferably fluoro, but may also be chloro, bromo or iodo.

A phenyl or naphthyl group may have one or more than one, preferably one or two of the same or different substituents as defined hereinbefore. Phenyl- or naphthyl-lower alkyl is e.g. benzyl, naphth-2-ylmethyl, 1- or 2-phenylethyl or 2- or 3-phenylpropyl, each optionally substituted as described hereinbefore.

Salts of the compounds of the formula I are particularly pharmaceutically acceptable salts thereof, such as the corresponding addition salts with acids, as well as the salts with bases. Suitable acids for the formation of acid addition salts are, for example, mineral acids, such as hydrochloric, hydrobromic, sulphuric or phosphoric acid, or organic acids, such as organic sulphonic acids, for example, benzenesulphonic, 4-toluenesulphonic or methanesulphonic acid, and organic carboxylic acids, such as acetic, lactic, palmitic, stearic, malic, maleic, fumaric, tartaric, ascorbic or citric acid. Salts with bases are, for example, alkali metal or alkaline earth metal salts, such as sodium, potassium, calcium or magnesium salts, or ammonium salts, such as those with ammonia or suitable organic amines, e.g. diethylamine, di-(2-hydroxyethyl)-amine or tri-(2-hydroxyethyl)-amine. The compounds of the formula I may also form inner salts.

Depending on the presence of asymmetric carbon atoms, the compounds of this invention may be in the form of mixtures of isomers, particularly racemates, or in the form of pure isomers, particularly optical antipodes.

It has been found that the compounds of the formula I and their pharmaceutically acceptable salts possess valuable pharmacological properties. They show an effective binding at the $GABA_B$-receptor and are found to act as antagonists on said receptor. Mechanistically, antagonism at $GABA_B$ receptors may increase the release of fast excitatory amino acid transmitters, i.e. glutamate and aspartate, thus improving information processing in the brain. In line with this is the finding that the late inhibitory postsynaptic potential in hippocampus, attributed to a $GABA_B$ mechanism, is shortened by the antagonists thus allowing a faster sequence of nerve impulse transfer.

On the other hand, chronic treatment with antidepressants and repetitive electroshock have been found to increase the number of $GABA_B$ receptors in rat cerebral cortex. In line with receptor theories, chronic treatment with $GABA_B$ antagonists should result in the same effect. For these and other reasons, $GABA_B$ antagonists may therefore act as antidepressants.

The $GABA_B$ antagonists of the present invention interact at the $GABA_B$ receptor with $IC_{50}$ values starting from about $10^{-7}$M (moles/liter) in rat brain cortex membranes. In contrast to $GABA_B$ agonists, such as baclofen, they do not potentiate the stimulation of adenylate cyclase in rat cerebral cortex slices by noradrenaline, but antagonize the effects of baclofen. The antagonism against baclofen has also been shown in in vitro electrophysiological models, such as the penicilline-induced "epileptic" hippocampal slice preparation, where baclofen, at a concentration of 6 $\mu$M inhibits "epileptic"-like discharges of pyramidal cells. The compounds of the invention antagonise the effects of baclofen at concentrations from approximately 10 to approximately 100 $\mu$M. In vivo, antagonism has been shown by ionophoresis of baclofen on rat cerebral cortex, and systemic application of antagonists in doses of 10-100 mg/kg. The muscle relaxant effects of baclofen measured in the rotarod model are also antagonized at doses of about 30 mg/kg i.p.

The antagonists do not only show antagonistic effects against baclofen, but have, as theoretically expected (see above), also effects on their own as antagonists of endogenous GABA. Thus the antagonists are active in behavioural models which are established in the art to be indicative of antidepressant, anxiolytic and/or nootropic properties. Compounds of the formula I have been found to be active, after peroral application, in the swim test according to Porsolt, in the Geller test, the one trial, step-down passive avoidance test (one-trial modification) in pretrial and posttrial situations, in the two compartment test and in the complex labyrinth. In addition, in studies on Rhesus monkeys, an increase in playfulness, exploration, social grooming and a reduction of signs of anxiety were observed. Accordingly, the compounds of formula I may be used as nootropic, antidepressant and anxiolytic agents. Of course, they may also be used as baclofen-antidotes.

The invention relates, for example, to compounds of the formula I, wherein either $R_1$ is halogen, $R_1'$ is halogen or hydrogen and $R_2$ and $R_2'$ denote hydrogen or $R_1$ and $R_1'$ represent hydrogen, $R_2$ is an aromatic radical and $R_2'$ is hydroxy or $R_2$ and $R_2'$ together represent oxo, or wherein R denotes an aliphatic, cycloaliphatic, cycloaliphatic-aliphatic or araliphatic radical having 2 or more carbon atoms, and to their salts, to a process for the manufacture of compounds of the formula I, to pharmaceutical containing the same and to their use as a medicament or for the manufacture thereof.

The invention relates in particular to compounds of the formula I, wherein $R_1$ is halogen, $R_1'$ is halogen or hydrogen and $R_2$ and $R_2'$ are hydrogen or $R_1$ and $R_1'$ are hydrogen, $R_2$ denotes lower alkyl, phenyl, phenyl mono- or disubstituted by halogen, lower alkyl, lower alkoxy and/or trifluoromethyl or pyridyl and $R_2'$ is hydroxy or $R_2$ and $R_2'$ together represent oxo, and wherein R denotes lower alkyl having 2 or more carbon atoms, lower alkenyl, lower alkynyl, a cycloalkyl, hydroxycycloalkyl, cycloalkyl-lower alkyl, cycloalkyl-(hydroxy)lower alkyl or lower alkylthiocycloalkyl-(hydroxy)-lower alkyl group having 3 to 6 ring carbon atoms, oxo-lower alkyl, amino-lower alkyl, lower alkanoylamino-lower alkyl, phthalimido-lower alkyl, mono- or dihydroxy-lower alkyl, hydroxy-lower alkenyl, amino-(hydroxy)lower alkyl, lower alkanoylamino-(hydroxy)lower alkyl, phthalimido-(hydroxy)lower alkyl, mono-, di- or polyhalogeno-lower alkyl, mono-, di- or polyhalogeno-lower alkenyl, mono-, di- or polyhalogeno-(hydroxy)lower alkyl, mono-, di- or polyhalogeno-(hydroxy)lower alkenyl, amino lower alkoxy-lwoer alkyl, lower alkylthio-lower alkyl, lower alkanesulphinyl-lower alkyl, lower alkanesulphonyl-lower alkyl, di-lower alkoxy-lower alkyl, di-lower alkylthio-lower alkyl, lower alkoxy-(hydroxy)lower alkyl, lower alkoxy-(halogeno)lower alkyl, phenyl-lower alkyl, phenyl-lower alkyl mono- or disubstituted, in the phenyl moiety, by halogen, lower alkyl, lower alkoxy and/or trifluoromethyl, naphthyl-lower alkyl, oxa- or thiacycloalkyl having 2 to 6 ring carbon atoms, or dioxa-, oxathia- or dithiacycloalkyl having 3 to 5 ring carbon atoms or, if $R_1$ and $R_1'$ denote hydrogen, $R_2$ represents phenyl, phenyl mono- or disubstituted by halogen, lower alkyl, lower alkoxy and/or trifluoromethyl or pyridyl and $R_2'$ is hydroxy, R represents methyl, and to their salts, especially pharmaceutically acceptable salts.

The invention relates in particular, for example, to compounds of the formula I, wherein $R_1$ is halogen, $R_1'$ is halogen or hydrogen and $R_2$ and $R_2'$ are hydrogen or $R_1$ and $R_1'$ are hydrogen, $R_2$ denotes phenyl or phenyl mono- or disubstituted by halogen, lower alkyl, lower alkoxy and/or trifluoromethyl and $R_2'$ is hydroxy or $R_2$ and $R_2'$ together represent oxo, and wherein R denotes lower alkyl having 2 or more carbon atoms, lower alkenyl, lower alkynyl, a cycloalkyl, hydroxycycloalkyl, cycloalkyl-lower alkyl, cycloalkyl-(hydroxy)lower alkyl or lower alkyl-thiocycloalkyl-(hydroxy)-lower alkyl group having 3 to 6 ring carbon atoms, oxo-lower alkyl, amino-lower alkyl, lower alkanoylamino-lower alkyl, phthalimido-lower alkyl, mono- or dihydroxy-lower alkyl, hydroxy-lower alkenyl, amino-(hydroxy)-lower alkyl, lower alkanoylamino-(hydroxy)lower alkyl, phthalimido-(hydroxy)lower alkyl, mono-, di- or polyhalogeno-lower alkyl, mono-, di- or polyhalogeno-lower alkenyl, mono-, di- or polyhalogeno-(hydroxy)-lower alkyl, mono-, di- or polyhalogeno-(hydroxy)-lower alkenyl, amino lower alkoxy-lower alkyl, lower alkylthio-lower alkyl, lower alkanesulphinyl-lower alkyl, lower alkanesulphonyl-lower alkyl, di-lower alkoxy-lower alkyl, di-lower alkylthio-lower alkyl, lower alkoxy-(hydroxy)lower alkyl, lower alkoxy-(halogeno)-lower alkyl, phenyl-lower alkyl, phenyl-lower alkyl mono- or disubstituted, in the phenyl moiety, by halogen, lower alkyl, lower alkoxy and/or trifluoromethyl, naphthyl-lower alkyl, oxa- or thiacycloalkyl having 2 to 6 ring carbon atoms, or dioxa-, oxathia- or dithiacycloalkyl having 3 to 5 ring carbon atoms, and to their salts, especially pharmaceutically acceptable salts.

The invention relates especially to compounds of the formula I, wherein either $R_1$ and $R_1'$ are fluoro and $R_2$ and $R_2'$ represent hydrogen or $R_1$ and $R_1'$ are hydrogen, $R_2$ is phenyl, phenyl substituted by halogen such as fluoro, $C_1$–$C_4$alkyl, such as methyl, $C_1$–$C_4$alkoxy such as methoxy, and/or trifluoromethyl and $R_2$ is hydroxy or $R_1$ and $R_1'$ are hydrogen and $R_2$ and $R_2'$ together represent oxo, and wherein R is $C_2$–$C_{12}$-alkyl, such as ethyl, butyl, isobutyl, pentyl or isopentyl, $C_2$–$C_7$-alkenyl, such as but-3-enyl, $C_2$–$C_7$-alkynyl, such as pent-3-ynyl, mono- or dihydroxy-$C_2$–$C_7$-alkyl, such as 2-(2-hydroxy)propyl, 2-(1,2-di-hydroxy)propyl, 2-(2-hydroxy)butyl or 1-hydroxybutyl, oxo-$C_3$–$C_7$alkyl, such as 3-oxobutyl, amino-$C_3$–$C_6$alkyl, such as 3-aminopropyl or 4-aminobutyl, phthalimido-$C_3$–$C_6$alkyl, such as 3-phthalimidopropyl or 4-phthalimidobutyl, or phthalimido-$C_3$–$C_7$(hydroxy)alkyl, such as 3-phthaloimido-2-hydroxypropyl or 4-phthalimido-2-hydroxy-butyl, and their salts, especially pharmaceutically acceptable salts.

Especially preferred are compounds of the formula I, wherein $R_1$ and $R_1'$ are fluoro and $R_2$ and $R_2'$ are hydrogen, or $R_1$ and $R_1'$ are hydrogen and $R_2$ and $R_2'$ together represent oxo, and wherein R denotes $C_2$–$C_7$-alkyl, such as ethyl, butyl or isobutyl, α-saturated $C_3$–$C_7$-alkenyl, such as but-3-enyl, α-saturated $C_3$–$C_7$-alkynyl, such as pent-3-ynyl, α-, β-, γ- or δ-hydroxy-$C_2$–$C_7$-alkyl, such as 2-(2-hydroxy)propyl or 1-hydroxybutyl, α,α-difluoro-$C_2$–$C_4$-alkyl, such as 1,1-difluorobutyl, mono-, di- or trifluoro-α-hydroxy-$C_3$–$C_7$-alkyl, such as 1-hydroxy-4,4,4-trifluorobutyl, α-saturated mono-, di- or trihalogeno-α-hydroxy-$C_3$–$C_7$-alkenyl, such as 1-hydroxy-2-fluoro-but-2-enyl, $C_1$–$C_4$-alkoxy-$C_1$–$C_4$-alkyl, such as 2-ethoxyethyl or 3-methoxypropyl, di-$C_1$–$C_4$-alkoxy-$C_1$–$C_4$-alkyl, $C_3$–$C_6$-cycloalkyl-$C_1$–$C_4$-alkyl, such as cyclopropyl-methyl, α-hydroxy-$C_3$–$C_6$-cycloalkyl, such as 1-hydroxycylobutyl, or $C_3$–$C_6$-cycloalkyl-α-hydroxy-$C_1$–$C_4$-alkyl, such as 1-cyclopropyl-1-hydroxymethyl, and to their salts, especially pharmaceutically acceptable salts.

Also preferred are compounds of the formula I, wherein $R_1$ and $R_1'$ are hydrogen, $R_2$ is phenyl, phenyl substituted by halogen such as fluoro, $C_1$–$C_4$alkyl, such as methyl, $C_1$–$C_4$alkoxy such as methoxy, and/or trifluoromethyl and $R_2'$ is hydroxy, and wherein R represents $C_1$–$C_7$-alkyl, such as methyl or n-, sec.- or isobutyl, and their salts, especially pharmaceutically acceptable salts.

In the preferred subgroups of compounds of the formula I specified hereinbefore, R most preferably denotes $C_3$–$C_4$alkyl, such as propyl, isopropyl or n-, sec.- or iso-butyl, or, if applicable, hydrogen or methyl.

Very especially preferred are the compounds of the formula I, wherein R is $C_2$–$C_7$-alkyl, such as n-, sec.- or iso-butyl, and wherein $R_1$ and $R_1'$ are fluoro and $R_2$ and $R_2'$ are hydrogen, or $R_1$ and $R_1'$ are hydrogen and $R_2$ and $R_2'$ together represent oxo, and pharmaceutically acceptable salts thereof.

Most preferred are the compounds of the formula I, wherein R is $C_3$–$C_7$-alkyl and wherein $R_1$ and $R_1'$ are fluoro and $R_2$ and $R_2'$ are hydrogen, or $R_1$ and $R_1'$ are hydrogen and $R_2$ and $R_2'$ together represent oxo, and pharmaceutically acceptable salts thereof.

The invention specifically relates to the compounds of the formula I described in the Examples herein, and to their salts, especially pharmaceutically acceptable salts.

The process for the manufacture of compounds of the formula I, is characterized in that a) in a compound of formula II

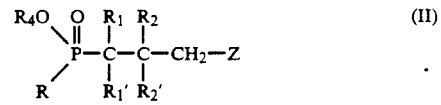

in which R, $R_1$, $R_1'$, $R_2$ and $R_2'$ have their previous significances, Z represents a protected or latent amino group $Z_0$ and $R_4$ denotes hydrogen or a hydroxy-protective group $R_5$, and wherein amino as a constituent of R and/or hydroxy $R_2'$ or oxo $R_2+R_2'$ may be present in a temporarily protected form, any group $R_5$ or $R_6$ is replaced by hydrogen and/or any group $Z_0$ is converted into —$NH_2$; or b) in a compound of the formula III

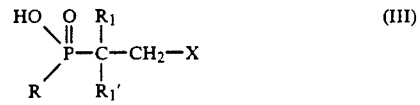

in which $R_1$ and $R_1'$ have their previous significances and X is a group capable of being converted into a group of formula —$CH_2NH_2$ (Ia), the group X is converted into a group of formula Ia; or c) a compound of formula IV

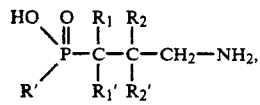

wherein R' may be selected from lower alkenyl, lower alkadienyl or lower alkynyl, to produce a compound of formula I, wherein R is lower alkyl, or from phenyl to produce a compound of formula I, wherein R is cyclohexyl, is reduced, and, if desired, a resulting salt obtained in this process may be converted into the free compound or into another salt and/or, if desired, a resulting free compound is converted into a salt to suit the above definition and/or, if desired, a resulting mixture of isomers is separated into the individual isomers.

Protected hydroxy groups such as groups —$OR_5$ present in a protected form in starting materials of the formula II are, for example, etherified hydroxy groups, such as hydroxy groups etherified with aliphatic, cycloaliphatic or araliphatic alcohol, e.g. with a lower alkanol, a cycloalkanol, or a phenyl- or diphenyl-lower alkanol, or hydroxy groups etherified with an aliphatic silanol, e.g. with a tri-lower alkyl silanol. As groups $R_5O$—, lower alkoxy, e.g. $C_1$–$C_4$-alkoxy, mono- or diphenyl-lower alkoxy, e.g. 1-phenyl- or 1,1-diphenyl-$C_1$–$C_4$-alkoxy, and tri-lower alkylsilyloxy, e.g. tri-$C_1$–$C_4$-alkyl-, such as trimethylsilyloxy, are especially preferred. Intermediarily protected hydroxy groups $R_2'$ are preferably hydroxy group etherified with an aliphatic silanol as specified hereinbefore.

Protected amino groups $Z_0$ as well as intermediarily protected amino groups as constituent of R in starting materials of the formula II are, for example, acylamino groups such as lower alkanoylamino, e.g. acetylamino, or phthalimido, lower alkoxycarbonylamino unsubstituted or substituted by phenyl, e.g. benzyloxycarbonylamino or tert.-butoxycarbonylamino groups, or 1-aryl-methylamino groups e.g. benzylamino, or 1-phenyl-lower alkylamino, silylated amino groups, such as tri-lower alkylsilylamino or especially bis-(tri-lower alkylsilyl)amino, e.g. bis-trimethylsilylamino. A latent amino group $Z_0$ may be e.g. nitro or azido.

Intermediarily protected oxo group $R_2+R_2'$ are preferably ketalised or thioketalised oxo group such as specified herinafter.

Preferred compounds of formula II are those having the formula IIa

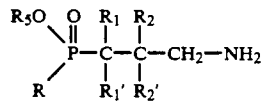

wherein $R_5$ represents a hydroxy-protective group, for example, $C_1$–$C_4$-alkyl or $C_1$–$C_4$-alkyl substituted by lower alkanoyloxy or by one or two optionally substituted phenyl groups, such as 1-$C_2$–$C_7$-alkanoyloxy-$C_1$–$C_4$-alkyl, e.g. pivaloyloxymethyl, or 1-phenyl- or 1,1-diphenyl-$C_1$–$C_4$-alkyl, e.g. benzyl, or having the formula IIb

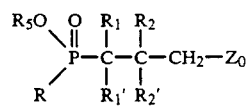

wherein $R_5$ represents a hydroxy-protective group, for example, $C_1$–$C_4$-alkyl, $C_1$–$C_4$-alkyl substituted by one or two optionally substituted phenyl groups, such as 1-phenyl- or 1,1-diphenyl-$C_1$–$C_4$-alkyl, e.g. benzyl, or a silyl group, such as tri-$C_1$–$C_4$-alkylsilyl, e.g. trimethylsilyl, and $Z_0$ has its previous significance and denotes, for example, $C_1$–$C_7$-alkanoylamino, e.g. acetylamido, phthalimido or bis-silylamino, such as bis(tri-$C_1$–$C_4$-alkylsilyl)amino, e.g. bis(trimethylsilyl)amino, or having the formula IIc

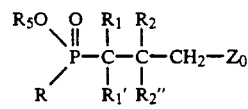

wherein $R_5$ represents a hydroxy-protective group, for example, $C_1$–$C_4$-alkyl, $C_1$–$C_4$-alkyl substituted by one or two optionally substituted phenyl groups, such as 1-phenyl- or 1,1-diphenyl-$C_1$–$C_4$-alkyl, e.g. benzyl, or a silyl group, such as tri-$C_1$–$C_4$-alkylsilyl, e.g. trimethylsilyl, and $R_2''$ is a silylated hydroxy group, such as trimethylsilyloxy, and wherein in formulae IIa, IIb and IIc R, $R_1$, $R_1'$, $R_2$ and $R_2'$ have their previous significances if not indicated otherwise.

The replacement of the protective group $R_5$ in compounds of formula II, IIa, IIb or IIc by hydrogen may be effected by treatment with a suitable basic or acidic agent such as an alkali metal hydroxide, e.g. sodium hydroxide, or lithium hydroxide, an alkali metal halide particularly bromide or iodide such as lithium bromide or sodium iodide, thiourea, an alkali metal thiophenolate such as sodium thiophenolate, or a protonic or Lewis acid, such as a mineral acid, e.g. hydrochloric acid or a tri-lower alkyl halosilane, e.g. trimethylchlorosilane. The replacement reaction may be carried out in the absence or presence of a solvent and, if necessary, while cooling or heating, in a closed vessel and/or under an atmosphere of an inert gas.

When $R_5$ denotes $C_1$–$C_4$-alkyl substituted in 1-position by one or two phenyl groups, e.g. when $R_5$ is benzyl, the replacement of such a group in compounds of formulae II, IIa or IIb by hydrogen may be effected by hydrogenolysis in the presence of a metallic hydrogenation catalyst, or any other suitable procedure.

Alternatively, the replacement of the protective group, e.g. of a silyl or, for example of an alkyl group, $R_5$ in compounds of formulae II, IIa, IIb or IIc by hydrogen may be effected by treatment with an acid under hydrolytic conditions, especially with a mineral acid such as a hydrohalic acid e.g. hydrochloric acid which is used in dilute or concentrated aqueous form, or by treatment with an organic silyl halide such as trimethylsilyl iodide or bromide, followed by hydrolysis, if necessary. The reaction is preferably conducted at elevated temperature e.g. while refluxing the reaction mixture and, if necessary using an organic diluent, in a closed vessel and/or under an atmosphere of an inert gas. The kind of replacement of the protective group $R_5$ depends e.g. on the substituent R present in a compound of formula II which must be retained in converting a compound of formula II to a compound of formula I. Said replacement may be effected e.g. according to the illustrating examples.

Protected amino group or latent amino groups $Z_0$ in compounds of formula II, IIb or IIc may be converted into free amino according to known methods, which are selected according to the characteristics of the protected or latent amino group to be converted into amino, such as solvolytic or hydrogenolytic procedures, for example, hydrolysis in the presence of an acid or a base, acidolysis, e.g. treatment with trifluoroacetic acid, treatment with hydrazine, or hydrogenolysis in the presence of a metallic hydrogenation catalyst, or any other suitable procedure.

Depending on the groups involved, the replacement and conversion operations may be carried out in any sequence or simultaneously by methods which are well known per se.

It is preferred that all protecting groups are converted, $R_5$ or hydroxy-protective groups of $R_2'$ being converted hydrogen and $Z_0$ being converted to $NH_2$, in a single step, by treatment with an acid, preferably a hydrohalic acid, especially hydrochloric acid, under hydrolytic conditions.

The compounds of formula II may be prepared, for example, by various methods according to the nature of the group X in the formula V defined hereinafter, e.g. by reacting, in the presence of a basic catalyst or in the presence of agents forming free radicals, a compound of the formula V

(V)

in which R and $R_5$ have their previous significance which can be prepared by reaction of a compound of the formula R—$PHal_2$ (Va; Hal=halogen) with an alcohol $R_5OH$ in the presence of a tri-lower alkylamine or, more advantageously, by reaction of aqueous hypophosphonous acid with an orthoester of the formula $C(C_1-C_4-alkyl)(OR_5)_3$ (Vb) yielding, in the latter case, a compound V, wherein R denotes $C(C_1-C_4-alkyl)(OR_5)_2$, with a compound of formula VI

(VI)

in which $R_1$ and $R_1'$ have their previous significance and X is a group capable of being converted into a group of formula —$CH_2Z$, wherein Z has its previous significance, in order to produce a compound of formula VII

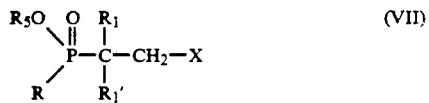

(VII)

wherein $R_1$, $R_1'$, $R_5$, R and X have their previous significances; and then converting the group X into a group of formula —$CH_2Z$.

A group X is primarily cyano but may also represent carbamoyl, a group of formula —$CH_2Z_0$ (VIIa) in which $Z_0$ has the previous significance; or X is a group of formula —CH=Y in which —C=Y is an optionally functionally modified carbonyl group such as a corresponding ketal or thioketal group, including a corresponding cyclic group.

The conversion of the group X into the group of the formula —$CH_2$—$NH_2$ is preferably effected in an analogous manner as described hereinafter for process variant b). If desired, said group may subsequently be reprotected by methods known per se into a group of the formula —$CH_2$—$Z_0$, wherein $Z_0$ has the meaning indicated.

The compounds of formula V are either known or they may be prepared by methods as described hereinbefore. Specific examples of compounds of formula V include: isopropyl (ethyl)phosphonite, isopropyl (n-propyl)-phosphonite, isobutyl (n-butyl)phosphonite, isobutyl (isopropyl)-phosphonite, isobutyl (isobutyl)-phosphonite and isobutyl (sec.-butyl)-phosphonite.

Likewise, compounds of formula VI are either known or can be obtained by methods which are well known.

Alternatively, a compound of the formula VIII

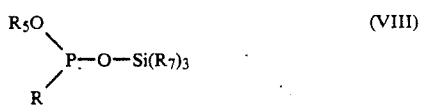

(VIII)

in which $R_5$ is $C_1$-$C_4$-alkyl or $C_1$-$C_4$-alkyl substituted by one or two phenyl residues or an additional group —$Si(R_7)_3$, each $R_7$, independently, is $C_1$-$C_6$-alkyl, preferably $C_1$-$C_2$-alkyl, particularly methyl, the groups $R_5$ and $R_7$ being the same or different, can be reacted with a compound of the formulae IXa, IXb or VI

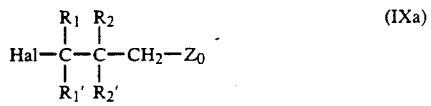

(IXa)

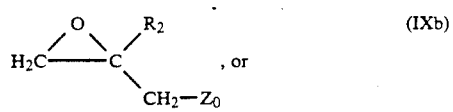

(IXb)

(VI)

in which $R_1$, $R_1'$, $R_2$, $R_2'$, $Z_0$ and X have their previous significances, X being primarily cyano or a group of the formula —CH=Y and Hal stands for halogen, such as iodo, bromo or chloro. The reaction with an epoxide of formula IXb is advantageously carried out in the presence of a mild Lewis acid, such as anhydrous zinc chloride, whilst the reactions with halides of formulae IXa or VI are preferably carried out under the conditions of the Arbusov method, e.g. at a reaction temperature ranging from room temperature to an elevated temperature, e.g. 160° C., while removing the trialkyl silyl halide formed in the reaction.

The compounds of formula IIb may also be prepared by reacting a compound of the formula a compound of formula X

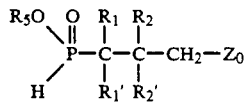

(X)

wherein $R_1$, $R_1'$, $R_2$, $R_2'$ and $Z_0$ have their previous significances and $R_5O$ denotes protected, e.g. esterified, hydroxy, with a silylating agent, such as a hexa-lower alkyl silazane or a tri-lower alkyl halosilane, e.g. with hexamethyldisilazane, or with trimethylchlorosilane, in the presence of triethylamine, to produce a compound of formula XI

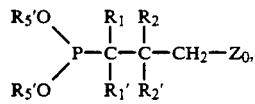

(XI)

wherein $R_5'$ denotes a group $R_5$ being tri-lower alkylsilyl, e.g. trimethylsilyl, and $Z_0$ denotes bis(tri-lower alkylsilyl)amino, such as bis(trimethylsilylamino).

The intermediate of the formula X or XI is then reacted with a compound capable of converting the

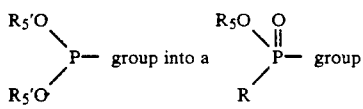

wherein R has its previous significance to produce a compound of formula IIb, in which $R_5$ has its previous significance. Thus, the intermediate of the formula X may be reacted, in the presence of a basic condensation agent, such as a tri-lower alkyl amine, e.g. of N-ethyl-N,N-diisopropyl-amine, with a corresponding halide, e.g. a lower alkyl halide of the formula R-Hal (XII, Hal=halogen), preferably under basic conditions, or may be reacted, for the manufacture of compounds IIb, in which R is an aliphatic, cycloaliphatic-aliphatic or araliphatic hydrocarbon radical having at least 2 carbon atoms in each of the aliphatic moieties, with a terminally unsaturated aliphatic, cycloaliphatic-aliphatic or araliphatic hydrocarbon having an terminal double bond between the carbon atom via which R is to be bonded to the P-atom and the adjacent carbon atom, or may be reacted, for the manufacture of compounds IIb, in which the carbon atom via which R is bonded to the P-atom is α-substituted by one hydroxy group, with a corresponding aliphatic, cycloaliphatic, cycloaliphatic-aliphatic or araliphatic aldehyde or ketone which corresponds, if the aldehyde or ketone functional group is replaced by one free valence and one hydroxy group, to the group R in the desired intermediate IIb.

Starting materials of formula X can be obtained starting from a compound of formula XIII or XIV

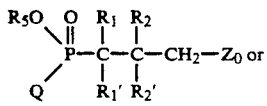

(XIII)

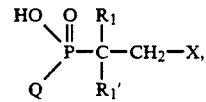

(XIV)

wherein Q is an α,α-di-lower alkoxy-lower alkyl group and $R_1$, $R_1'$, $R_2 R_2'$, X and $Z_0$ have their previous significance, the respective protecting groups $R_5$ and $Z_0$, or $R_5$ and X, respectively, being retained, when the compound of formula XIII or XIV is treated with a protic anhydrous medium.

Examples of such protic anhydrous media include: anhydrous hydrogen chloride gas, or an anhydrous medium may be generated from an organic compound having one or more Si—Cl bonds together with an agent e.g. an alkanol capable of cleaving the Si—Cl bond, to produce an anhydrous protic medium in situ.

Preferred anhydrous protic media include therefore trimethyl silyl chloride in dichloromethane/ethanol or in technical chloroform which contains ethanol.

The group Q preferably has the formula —C($R_8$)—C-($OR_9$)($OR_{10}$) (XV) in which $R_8$ denotes lower alkyl and $R_9$ and $R_{10}$, independently of one another, represent lower alkyl or together represent lower alkylene.

This process for the manufacture of compounds of the formula X is preferably carried out at a temperature ranging from −80° C. to 100° C., preferably from 0° C.-50° C.

While the relative molar ratios of the reactants i.e. of reactant XII or XIV to the organic silyl chloride, used may vary within a wide range, it is preferred to use molar ratios ranging from 1 to 2 molar equivalents of the latter, per molar equivalent of XII or XIV.

Compounds of the formula IIb, wherein $R_1$ and $R_1'$ denote hydrogen, $R_2$ denotes hydroxy and $R_2'$ represents hydrogen or $R_2$ and $R_2'$ together denote oxo, may also be produced by reacting a compound having the formula XV

(XV)

in the form of the salt of the formula XV'

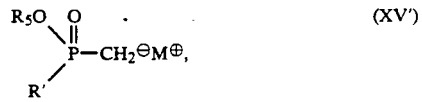

(XV')

wherein $R_5$ has its previous significance and R' is an aliphatic, cycloaliphatic or cycloaliphatic-aliphatic hydrocarbon radical, and M is an alkali metal, alkaline earth metal or transition metal, preferably lithium, sodium or potassium, calcium, zinc or tin, with a compound having the formula XVI

(XVI)

wherein $R_{5d}$ denotes a hydroxy protective group such as specified in formula IIb for $R_5$, halogeno, such as chloro or bromo, or hydrogen and $Z_0$ has its previous significance, to produce a compound having the formula IIb wherein $R_5$ is $R_{5d}$, R is R', $R_1$ and $R'_1$ denote hydrogen, $R_2$ is hydroxy and $R_2'$ denotes hydrogen or $R_2$ and $R_2'$ together denote oxo.

Intermediates of the formula IIc in which $R_1$ and $R_1'$ represent hydrogen, $R_2$ denotes an aromatic radical and $R_2'$ is a silylated hydroxy group, are preferably prepared by a novel process reacting hypophosphonous acid of formula XVII with propargyl alcohol of formula XVIII

 (XVII)

 (XVIII)

in an araliphatic hydrocarbon solvent, such as toluene, to give a compound of the formula XIX

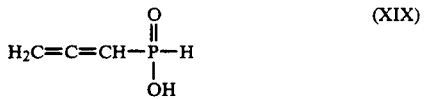 (XIX)

which, on reaction first with a haloformic acid lower alkyl ester of the formula Hal—COOR$_5$ (XX), wherein Hal denotes halo and R denotes lower alkyl, such as ethyl chloroformate, in the presence of a tri-lower alkylamine, such as triethylamine, and subsequently with an orthoacetic acid tri-lower alkylester, such as triethyl orthoacetate, in the presence of a Lewis acid, such as boron trifluoride, at 0° to 30° C., yields a compound of the formula XXI

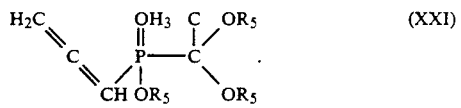 (XXI)

The compound of the formula XXI is then reacted with compound of the formula R$_2$—M (XXII), wherein M denotes a metallic group, such as a halomagnesium group, for example, the iodomagnesium group and copper-I-bromide/dimethylsulphide complex, preferably in dimethylsulphide/diethyl ether at −10° to −30° C., giving a compound of the formula XXIII

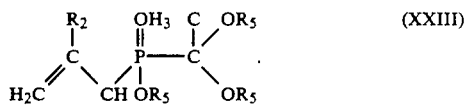 (XXIII)

The P-protecting group is removed as described hereinbefore, preferably by action of trimethylsilyl chloride in an approximately 9:1 mixture of dichloromethane and ethanol, and, without isolation reacted subsequently with butyl lithium in tetrahydrofuran at −60° to −80° and a compound of the formula R—Hal (XXIV), wherein R has the meanings indicated and Hal denotes a halogen atom to give a compound of the formula XXV

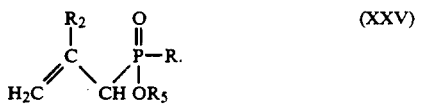 (XXV)

The product obtained from the reaction of tertiary butyl urethane and tertiary butyloxychloride in the presence of sodium hydroxide in a lower alkanol is then reacted with the intermediate of formula XXV in the presence of osmium tetroxide and silver nitrate in a mixture of acetonitrile, water and tertiary butanol, to form a compound of the formula IIc in which R$_5$, R$_1$, R$_1$', R$_2$ and R$_2$" have the meanings indicated. This intermediate can be converted into the corresponding compound of the formula I, for example, by reaction with a trimethylsilyl halide, such as trimethylsilyl bromide, in dichloromethane, and then treatment with aqueous methanol and subsequently with propylene oxide in ethanol.

In a preferred embodiment of process variant a) for the manufacture of compounds of formula I a compound of the formula IIa

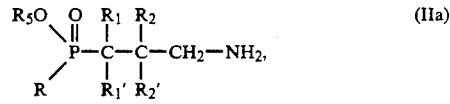 (IIa)

wherein R$_5$ denotes lower alkyl and R, R$_1$, R$_1$', R$_2$ and R$_2$' have their previous significances, is subjected to basic or acidic hydrolysis or is treated with a tri-lower alkyl halosilane.

In starting materials of the formula III for process variant b) X is primarily cyano but may also represent carbamoyl, a group of formula —CH$_2$Z$_0$ (VIIa) in which Z$_0$ has the previous significance; or X is a group of formula —CH=Y in which —C=Y is an optionally functionally modified carbonyl group such as a corresponding ketal or thioketal group, including a corresponding cyclic group.

When, in a compound of formula III X is an activating group X$_a$ such as cyano or —CH=O, then either a basic catalyst or a free radical catalyst may be employed. When, however, X is e.g. a residue of formula —CH$_2$Z$_0$, then free radical catalysts are required.

A basic catalyst used in the first step may be e.g. an alkali metal C$_1$-C$_4$-alkoxide, for example, a sodium or potassium C$_1$-C$_4$-alkoxide, in particular sodium methoxide, sodium ethoxide or potassium tert.-butoxide, an alkaline or alkaline earth metal fluoride, such as potassium fluoride or caesium fluoride, or an alkali metal hydride, such as sodium hydride. The reaction may be effected with or without the use of an added solvent. If a solvent is added, this is preferably an alcohol, in particular a C$_1$-C$_4$-alkanol corresponding to the alkoxide used as basic catalyst. The reaction temperature may vary from 0° C. to the boiling point of any added solvent.

Agents forming free radicals are, for example, compound convertible into free radicals by ionizing or ultraviolet radiation, preferably peroxy compounds, such as inorganic peroxy compounds, e.g. hydrogen peroxide or ammonium persulphate, or organic peroxides, e.g. benzoyl peroxide or tert.-butyl peroxide, or organic azo compounds, e.g. azo-bis-isobutyronitrile. Reactions involving free radical-forming agents may be conducted in the optional presence of a solvent and, if necessary, while cooling or heating, in a closed vessel and/or in an atmosphere of an inert gas.

The conversion of a group X into the group —CH$_2$—NH$_2$ is carried out according to known methods. Cyano and carbamoyl are converted into aminomethyl by reduction, cyano, for example, by hydrogenation in the presence of a suitable catalyst, e.g. Raney nickel and of a solvent, such as ethanol, which may preferably contain ammonia, and carbamoyl, for example, by treatment with a suitable hydride reducing agent, such as borane in tetrahydrofuran.

The conversion of a group —CH=Y, in which Y is oxygen, into the group of the formula —CH$_2$—NH$_2$ is carried out by known reductive amination procedures, e.g. treatment with sodium cyanoborohydride in the presence of ammonium acetate in a suitable solvent, such as dioxane, and while cooling, e.g. at about 0° C.

These reactions are carried out according to known methods, in the absence or presence of a solvent, which may also serve as a reagent, if necessary, while cooling or heating, in a closed vessel and/or in the atmosphere of an inert gas.

The compounds of formula III may be prepared in an analogous manner as described hereinbefore for the preparation of intermediates of the formula VII. For example, compounds of the formula III, wherein $R_2$ and $R_2'$ are hydrogen and R, $R_1$, $R_1'$ and X have the meanings indicated, can be obtained e.g. by reacting, in the presence of a basic catalyst or in the presence of agents forming free radicals, a compound of the formula V

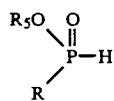
(V)

in which R and $R_5$ have their previous significance, with a compound of formula VI

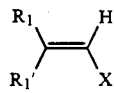
(VI)

in which $R_1$, $R_1'$ and X have their previous significance, and subsequently removing the O-protecting group $R_5$, for example, as described hereinbefore under process variant a) in order to produce a compound of formula III.

In a variation of this process, suitable for the preparation of compounds of the formula III, wherein R has the meaning indicated, $R_1$ and $R_1'$ denote hydrogen, $R_{2a}$ denotes a aliphatic, cycloaliphatic, cycloaliphatic-aliphatic or aromatic hydrocarbon radical and X denotes carbamoyl, the compound of the formula V is O-protected, for example, by means of trimethylsilyl chloride and then reacted with a corresponding epoxide of the formula XXVI

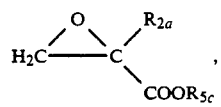
(XXVI)

wherein $R_{5c}$ represents lower alkyl, forming a compound of the formula XXVII

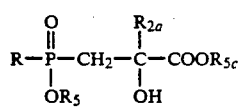
(XXVII)

which is then reacted with ammonia in a lower alkanol, such as ethanol, in the presence of an alkali metal cyanide, such as sodium cyanide. Subsequently, the group $R_5$ is split off to give the corresponding compound of the formula III, wherein $R_1$ and $R_1'$ denote hydrogen, $R_2$ is a group $R_{2a}$, $R_2'$ is hydroxy and X denotes carbamoyl.

Alternatively, a compound of the formula VIII

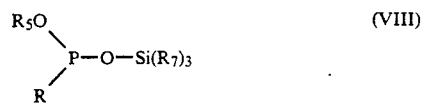
(VIII)

in which $R_5$ is $C_1$–$C_4$-alkyl or $C_1$–$C_4$-alkyl substituted by one or two phenyl residues or an additional group —Si(R$_7$)$_3$, each $R_7$, independently, is $C_1$–$C_6$-alkyl, preferably $C_1$–$C_2$-alkyl, particularly methyl, the groups $R_5$ and $R_7$ being the same or different, can be reacted with a compound of the formulae XXVIIIa, XXVIIIb

(XXVIIIa)

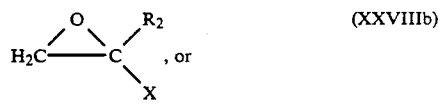
(XXVIIIb)

(VI)

in which $R_1$, $R_1'$, $R_2$, $R_2'$ and X have their previous significances, X being primarily cyano or a group of the formula —CH=Y, and Hal stands for halogen, such as iodo, bromo or chloro. The reaction with an epoxide of formula XXVIIIb is advantageously carried out in the presence of a mild Lewis acid, such as anhydrous zinc chloride, whilst the reaction with halides of formulae XXVIIIa is preferably carried out under the conditions of the Arbusov method, e.g. at a reaction temperature ranging from room temperature to an elevated temperature, e.g. 160° C., while removing the trialkyl silyl halide formed in the reaction.

The reduction of compounds of the formula IV according to process variant c) may be effected by any suitable reducing agent, such as hydrogen in the presence of a catalyst, for the reduction of aryl e.g. Raney nickel or Nishimura catalyst and for the reduction of aliphatic multiple bonds e.g. Palladium on charcoal, in the presence or absence of a solvent and at room temperature or elevated temperature.

The compounds of formula IV may be produced according to any of the methods described herein for the manufacture of compounds of formula I starting from starting materials having the respective unsaturated substituent R' instead of R. Furthermore, compounds of formula IV may also be obtained starting from the corresponding R'-dichlorophosphine by reaction with a lower alkanol, such as ethanol, and a tri-lower alkylamine, such as triethylamine, reacting the resulting R'-phosphonous acid ester with a compound of formula VI

(VI)

and converting the group X into the corresponding group —CH$_2$—NH$_2$.

Alternatively, a compound of the formula XXIX

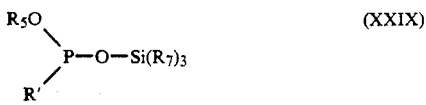

in which $R_5$ is $C_1$-$C_4$-alkyl or $C_1$-$C_4$-alkyl substituted by one or two phenyl residues or an additional group —$Si(R_7)_3$, each $R_7$, independently, is $C_1$-$C_6$-alkyl, preferably $C_1$-$C_2$-alkyl, particularly methyl, the groups $R_5$ and $R_7$ being the same or different, can be reacted with a compound of the formulae IXa, IXb or VI

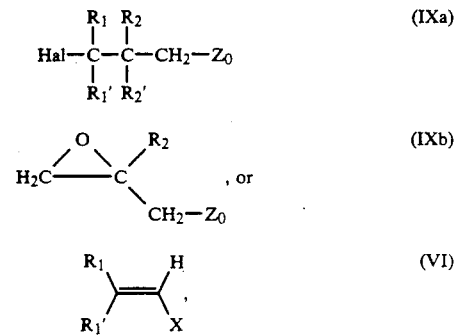

in which $R_1$, $R_1'$, $R_2$, $R_2'$, $Z_0$ and X have their previous significances, X being primarily cyano or a group of the formula —CH=Y and Hal stands for halogen, such as iodo, bromo or chloro. The reaction with an epoxide of formula IXb is advantageously carried out in the presence of a mild Lewis acid, such as anhydrous zinc chloride, whilst the reactions with halides of formulae IXa or VI are preferably carried out under the conditions of the Arbusov method, e.g. at a reaction temperature ranging from room temperature to an elevated temperature, e.g. 160° C., while removing the trialkyl silyl halide formed in the reaction.

In either process, the amino group is set free from a protected amino group $Z_0$ and, if present, the hydroxy group is set free from a protected hydroxy group in order to obtain the corresponding compound of the formula IV.

All above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures preferably near the boiling point of the solvents used, at atmospheric or super-atmospheric pressure.

Compounds of the formula I obtainable according to the process of the invention may be interconverted into another.

Thus, compounds of formula I, wherein R is substituted by hydroxy, and/or $R_2'$ denotes hydroxy, can be converted into the corresponding hydroxy-free compounds, for example, by reacting with thiocarbonyldiimidazole and treating the resulting imidazolylthiourethane in the presence of a radical-initiator, such as azoisobutyronitrile, with a tri-lower alkyl-stannane, e.g. with $(C_4H_9)_3SnH$, for example in benzene at 60° to 80° C.

Also double and/or triple bonds present in the group R may be reduced to single bonds, triple bonds also to double bonds to yield the corresponding less unsaturated compound of formula I.

The invention further includes any variant of the present processes, in which an intermediate product obtainable at any stage thereof is used as starting material and the remaining steps are carried out, or in which the starting materials are formed under the reaction conditions, or in which the reaction components are used in the form of their salts or optically pure antipodes. Whenever desirable, the above processes are carried out after first suitably protecting any. potentially interfering reactive functional groups, e.g. as illustrated herein.

Advantageously, those starting materials should be used in said reactions that lead to the formation of those compounds indicated above as being preferred.

The invention also relates to novel starting materials, especially to those leading to the preferred compounds of the formula I, and to processes for their manufacture.

Depending on the choice of starting materials and methods, the new compounds may be in the form of one of the possible isomers, for example, as diastereomers, as optical isomers (antipodes), as racemates, or as mixtures thereof.

In case diastereomeric mixtures of the above compounds or intermediates are obtained, these can be separated into the single racemic or optically active isomers by methods in themselves known, e.g. by fractional distillation, crystallization or chromatography.

The racemic products of formula I or basic intermediates can be resolved into the optical antipodes, for example, by separation of diastereomeric salts thereof, e.g., by the fractional crystallization of d- or l-(tartrate, dibenzoyltartrate, mandelate or camphorsulphonate) salts. Advantageously, the more active of the antipodes of the compounds of this invention is isolated.

Furthermore, the compounds of the invention are either obtained in the free (Zwitterion-) form, or as a salt thereof. For example, any resulting free compound can be converted into a corresponding acid addition salt, preferably with the use of a pharmaceutically acceptable acid or anion exchange preparation, salts with bases by treatment of the free compounds with bases or suitable cation exchange techniques, or resulting salts can be converted into the corresponding free compounds, for example the acid addition salts, with the use of a stronger base, such as a metal or ammonium hydroxide, or any basic salt, e.g., an alkali metal hydroxide or carbonate, or a cation exchange preparation and the salts with bases by treatment with suitable acidic reagents. These or other salts, for example, the picrates, can also be used for purification of the compounds obtained; the compounds are then first converted into salts. In view of the close relationship between the free compounds and the compounds in the form of their salts, whenever a compound is referred to in this context, a corresponding salt is also intended, provided such is possible or appropriate under the circumstances and the term "salts" shall, if desired also include the free compounds, where appropriate according to meaning and purpose.

The compounds, including their salts, may also be obtained in the form of their hydrates, or include other solvents used for the crystallization.

The present invention also relates to the use of the compounds of the invention for the preparation of pharmaceutical compositions, especially pharmaceutical compositions having selective $GABA_B$-antagonistic activity which can be used for the treatment of e.g. cognitive and memory disorders, depressive states of mind and anxieties.

The pharmaceutical compositions according to the invention are those suitable for enteral, such as oral or rectal, and parenteral administration to mammals, including man, for the treatment of diseases responsive to $GABA_B$-receptor blocking as given above, comprising an effective $GABA_B$-receptor blocking amount of a compound of the invention, alone or in combination with one or more pharmaceutically acceptable carriers.

The pharmacologically active compounds of the invention are incorporated into pharmaceutical compositions comprising an effective amount thereof in conjunction or admixture with excipients or carriers suitable for either enteral or parenteral application.

Preferred are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salts and/or polyethylene glycol; for tablets also c) binders, e.g. magnesium aluminium silicate, starch paste, gelatin, tragacanth, methylcellulose, sodium carboxymethylcellulose and/or polyvinylpyrrolidone; if desired, d) disintegrants, e.g. starches, agar, alginic acid or its sodium salt, or effervescent mixtures; and/or e) absorbents, colourants, flavours and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, the compositions may also contain other therapeutically valuable substances. Said compositions are prepared according to conventional mixing, granulating or coating methods, respectively, and contain about 0.1 to 75%, preferably about 1 to 50%, of the active ingredient.

The present invention also relates to the use of compounds of the invention having $GABA_B$-antagonistic properties and pharmaceutical compositions comprising said compounds for the treatment in mammals of disorders responsive to selective $GABA_B$-receptor blocking, particularly cognitive and memory disorders, and also of depressions and anxieties.

One aspect relates advantageously to the method of treatment of nootropic disorders in mammals, using an effective amount of a compound of the invention, preferably in the form of above-cited pharmaceutical compositions.

The dosage of active compound administered is dependent on the species of warm-blooded animal (mammal), the body weight, age and individual condition, and on the form of administration.

A unit dosage for a mammal of about 50 to 70 kg may contain between about 10 and 500 mg of the active ingredient.

The following examples are intended to illustrate the invention and are not to be construed as being limitations thereon. Temperatures are given in degrees Centigrade. If not mentioned otherwise, all evaporations are performed under reduced pressure, preferably between about 2 and 13 kPa. The structure of final products, intermediates and starting materials is confirmed by analytical methods, e.g. microanalysis and spectroscopic characteristics (e.g. MS, IR, NMR). The compounds of formula I are hereinafter referred to as 3-amino-1-$R_1$-1-$R_1'$-2-$R_2$-2-$R_2'$-propyl(R)-phosphinic acids.

EXAMPLE 1

A solution of 0.642 g of ethyl 3-(N-tert.-butoxycarbonylamino)-2-oxo-propyl(n-butyl)phosphinate in 10 ml of anhydrous dichloromethane under an inert atmosphere is treated with 1.53 g of trimethylbromosilane. After stirring for 7 hours at room temperature the volatile material is removed in vacuo to afford a pale yellow oil. This oil is dissolved in methanol containing 1% of water, and the clear pale yellow solution is stirred overnight at room temperature. The solvent is removed in vacuo to afford 3-amino-2-oxo-propyl(n-butyl)phosphinic acid hydrobromide, m.p. 135°-138°. Suspension in ethanol and treatment with propylene oxide affords 3-amino-2-oxo-propyl(n-butyl)phosphinic acid of m.p. 128°-130°.

The starting material may be prepared as follows.

A suspension of 8.0 g of sodium hydride (55% dispersion in oil) in 35 ml of anhydrous tetrahydrofuran under an inert atmosphere is treated with 35 ml of an anhydrous tetrahydrofuran solution of 25 g of ethyl n-butylphosphinate. The resulting suspension is stirred at room temperature for 1 hour before dropwise addition of 32 ml of methyl iodide. After 3 hours stirring at room temperature 10 ml of water are carefully added followed by 200 ml of dichloromethane. Separation of the organic layer, drying over anhydrous magnesium sulphate and removal of the solvent in vacuo affords an oil. Kugelrohrdistillation at 90° and $10^{-1}$ mbar affords ethyl n-butyl-(methyl)phosphinate.

A solution of 5.82 g of lithium diisopropylamide in 30 ml of anhydrous tetrahydrofuran is cooled to $-78°$ C. under an inert atmosphere. Under constant stirring at $-78°$ a solution of 9.84 g of ethyl n-butyl(methyl)phosphinate in 20 ml of anhydrous tetrahydrofuran is added over 15 minutes under a positive pressure of an inert atmosphere via a canula. The resulting pale yellow solution is stirred for 1 hour at $-78°$ and a pre-cooled ($-78°$ C.) solution of 1.89 g of N-tert.-butoxycarbonylglycine methyl ester in 10 ml of anhydrous tetrahydrofuran is added over 5 minutes via a canula. Thin layer chromatography indicates complete reaction after circa 10 minutes. At $-78°$ 4.0 g of glacial acetic acid is added and the mixture is allowed to warm to room temperature. The reaction mixture is diluted with dichloromethane and washed with water. Drying over magnesium sulphate and removal of the solvent in vacuo affords a pale yellow oil. Removal of the excess starting material by distillation and chromatography of the resulting yellow oil on silica gel yields ethyl 3-(N-tert.-butoxycarbonylamino)-2-oxo-propyl(n-butyl)-phosphinate as a colourless viscous oil.

EXAMPLE 2

A solution of 1.2 g of ethyl 3-amino-2-(4-chlorophenyl)-2-hydroxy-propyl(n-butyl)phosphinate hydrochloride in 5 ml of ethanol is treated with 0.24 g of sodium hydroxide dissolved in 3 ml of water. The solution heated to 60° for 20 hours. After this time the solution is cooled to room temperature and washed 2-times with 50 ml each of dichloromethane and once with 50 ml of diethyl ether. The aqueous phase is evaporated to dryness. The residue is suspended in n-propanol, heated to 80° C. for 10 minutes and filtered. The n-propanol is removed in vacuo to afford a white solid. Chromatography on reverse-phase silica gel followed by drying in vacuo at 80° yields sodium 3-amino-2-(4-chlorophenyl)-2-hydroxy-propyl(n-butyl)phosphinate; m.p. 215°-215.5°; 1H-NMR spectrum (D$_2$O): δ=7.4 ppm (4H, s), 2.91 ppm (2H, ABq), 2.22 ppm (2H, ABq,d), 1.37-1.0 ppm (6H, m), 0.75 ppm (3H, t).

The starting material may be obtained as follows:

To a solution of 19.6 g of methyl 2-(4-chlorophenyl)acrylate in 200 ml of dry chloroform, under an inert atmosphere are added 47.06 g of 55% m-chloroperbenzoic acid and the resulting solution is refluxed for 18 hours. The mixture is then cooled and the solid removed by filtration. Evaporation in vacuo of the filtrate and chromatography of the residue on silica-gel affords methyl 2-(4-chlorophenyl)-2,3-epoxy-propionate as a colourless oil.

A solution of 4.5 g of ethyl n-butylphosphinate in anhydrous tetrahydrofuran containing 3.79 g of triethylamine is treated under an inert gas with an anhydrous tetrahydrofuran solution of 4.07 g of trimethylchlorosilane. A white precipitate forms immediately and the resulting suspension is stirred at room temperature under an inert gas for 24 hours. The reaction mixture is then filtered under an inert gas and the filtrate is concentrated in vacuo to afford a cloudy oil which is then treated with 2.58 g of methyl 2-(4-chlorophenyl)-2,3-epoxy-propionate and 0.5 g of anhydrous zinc chloride. An exothermic reaction results. After the exothermia has subsided, the clear solution is heated slowly to 70° and stirred at this temperature for 6 more hours after which time chromatographic analysis indicates completeness of the reaction. The reaction mixture is cooled to room temperature, diluted with dichloromethane and washed with water. Drying of the organic layer over anhydrous magnesium sulphate and removal of the solvent in vacuo affords an oil. The excess starting material is removed by Kugelrohr-distillation in high vacuum and the pale yellow residue is chromatographed on silica-gel to yield methyl 2-(4-chlorophenyl)-2-trimethylsilyloxy-3-(O-ethyl-P-n-butyl-phospinyl)-propionate as a viscous, colourless oil.

To a solution of 9.16 g of methyl 2-(4-chlorophenyl)-2-trimethylsilyloxy-3-(O-ethyl-P-n-butyl-phosphinyl)-propionate in 70 ml of absolute ethanol are added 0.103 g of sodium cyanide followed by 20 g of liquid ammonia. The resulting mixture is heated in an autoclave for 20 hours at 50° and 12 bar. The ammonia is removed under water pump vacuum and the ethanol is moved by rotary evaporation to afford a light brown-coloured oil. Chromatography on silica-gel affords 2-(4-chlorophenyl)-2-hydroxy-3-(O-ethyl-P-n-butylphosphinyl)-propionamide as an oily solid with an ill defined melting point of circa 100°.

A solution of 1.04 g of 2-(4-chlorophenyl)-2-hydroxy-3-(O-ethyl-P-n-butylphosphinyl)-propionamide in 10 ml of anhydrous tetrahydrofuran is heated to reflux and treated with 0.69 g of borane/dimethyl sulphide complex over 15 minutes while collecting the liberated dimethyl sulphide by distillation. Reflux is continued for 4 hours and the reaction mixture cooled to room temperature and treated with 0.85 g of absolute methanol. After addition is complete the reaction is stirred for a further 30 minutes before cooling to 0° and addition of 1.19 ml of a 2.0 m solution of hydrogen chloride in absolute ether. The solvent is then removed to afford ethyl 3-amino-2-(4-chlorophenyl)-2-hydroxy-propyl(n-butyl)-phosphinate hydrochloride as a hygroscopic, glassy white solid.

EXAMPLE 3

A solution of 5.0 g of 2-cyano-1-fluoro-ethenyl(n-butyl)phosphinic acid and 10 ml of liquid ammonia in 150 ml of absolute ethanol is treated with 0.75 g of 5% rhodium on charcoal. The suspension is shaken under hydrogen (20 bars) at 20° C. until thin-layer chromatography indicates complete reaction. The catalyst is removed by filtration and the filtrate is evaporated in vacuo to give a solid. Crystallisation from ethanol/acetone affords 3-amino-1-fluoro-propyl(n-butyl)phosphinic acid.

The starting material may be obtained as follows:

24 g of sodium hydride (55% dispersion in oil) is washed with hexane and suspended in 100 ml of absolute tetrahydrofuran under an inert atmosphere. A solution of 104.4 g of ethyl diethoxymethylphosphinate in 100 ml of anhydrous tetrahydrofuran is added dropwise maintaining the temperature at 20°. The reaction is exothermic and gas evolution results. After the addition is complete, stirring is continued for 1.5 hours before adding 209.7 g of n-butylbromide at 20°. Finally, the suspension is stirred for 2.5 hours, cooled in an ice/water bath and water is added carefully. The mixture is concentrated in vacuo and the residue partitioned between dichloromethane and water. Drying of the organic layer over sodium sulphate and removal of the solvent affords a colourless oil. Distillation in high vacuo affords ethyl diethoxymethyl(n-butyl)-phosphinate; b.p. 71.5°-74° (10$^{-3}$ mbar).

109 g of ethyl diethoxymethyl(n-butyl)phosphinate are dissolved in 160 ml of 4.0 m aqueous hydrochloric acid. The clear solution is warmed to reflux for 24 hours, then cooled to room temperature and washed with diethyl ether. Evaporation of the aqueous layer affords n-butylphosphonous acid as an oil. This oil is dried in high vacuo. A former sample is obtained by washing the ether extracts with hexane followed by water and evaporation of the aqueous layer.

A suspension of 12.2 g of n-butylphosphonous acid in 50 ml of hexamethyldisilazane is heated to reflux under an inert atmosphere for 24 hours. The excess hexamethyldisilazane is removed by distillation at atmospheric pressure. To the residue are added 4.45 g of 3,3-difluoro-acrylonitrile. The reaction mixture is stirred at room temperature for 20 hours followed by heating 50° C. for 2 hours. After cooling to room temperature, the mixture is diluted with dichloromethane and washed with water. The organic layer is dried over sodium sulphate and evaporated in vacuo to afford 2-cyano-1-fluoro-ethenyl(n-butyl)phosphinic acid as an oil which can be used without further purification.

EXAMPLE 4

A solution of 1.0 g of ethyl-3-(N-tert.-butoxycarbonylamino)-2-oxopropyl(cyclohexylmethyl)phosphinate in 15 ml of anhydrous dichloromethane under an inert atmosphere at room temperature is treated with 2.1 g of trimethylbromosilane. After stirring for 7 hours the volatile components are removed under reduced pressure to give a pale yellow oil. This oil is dissolved in methanol containing 1% of water and the clear pale yellow solution is stirred overnight at room temperature. The solvent is removed under reduced pressure to afford 3-amino-2-oxo-propyl(cyclohexylmethyl)phosphinic acid hydrobromide, m.p. 180°-182° C. Suspension in ethanol and treatment with propylene oxide affords 3-amino-2-oxo-propyl(cyclohexylmethyl)phosphinic acid, $^1$H-NMR (D$_2$O): δ (ppm)=4.15 (2H, s, CH$_2$N), 3.10 (2H, d, J=15 Hz, CH$_2$—P), 1.80 (2H, m, P—CH$_2$), 1.73-1.52 (5H, m, 2×CH$_2$+CH), 1.34-0.95 (6H, m, 3×CH$_2$).

The starting material may be prepared as follows:

A suspension of 16.5 g of sodium hydride (80% in oil) in 100 ml of anhydrous tetrahydrofuran under an inert atmosphere at 20° is treated with 100 ml of an anhydrous tetrahydrofuran solution of 104.4 g of ethyl (diethoxymethyl)phosphinate at such a rate so that the temperature does not exceed 25°. After the addition is complete, the resulting suspension is stirred for 1 hour at room temperature. This suspension is then treated with 85.5 g of benzylbromide and the reaction mixture stirred overnight at room temperature. The reaction mixture is then cooled in an ice/water bath and 200 ml of water are carefully added. The clear solution is then partitioned between dichloromethane and water. Separation of the dichloromethane layer followed by drying and removal of the solvent affords a pale yellow oil. Distillation in high vacuum affords ethyl-P-benzyl-P-diethoxymethylphosphinate of b.p. 105°-125° (10$^{-2}$ mbar); $^1$H-NMR (CDCl$_3$): δ (ppm)=7.29 (5H, m, Ph), 4.58 (1H, d, J=9 Hz, CHP), 4.08 (2H, q, CH$_2$OP), 3.83 and 3.66 (4H, m, 2×CH$_2$OC), 3.21 (2H, AB$_q$J=15×6.0 Hz, CH$_2$Ph), 1.23 (9H, m, 3×CH$_3$).

A solution of 4.29 g of ethyl P-benzyl-P-diethoxymethyl phosphinate in 42 ml of absolute ethanol is treated with 10 g of Raney nickel and the suspension hydrogenated at 100°-110° C. and 120 bar for 34 hours. The catalyst is removed by filtration and the residue washed with absolute ethanol. The combined filtrate and washings are concentrated in value to afford an oil. Distillation in high vacuum affords O-ethyl-P-cyclohexylmethyl-P-diethoxymethylphosphinate; b.p. 103°-105° (10$^{-2}$ mbar); $^1$H-NMR (CDCl$_3$): δ (ppm)=4.62 (1H, d, J=9 Hz, CHP), 4.17 (2H, m, CH$_2$OP), 3.84 and 3.69 (4H, m, 2×CH$_2$OC), 1.88 (3H, m, CH$_2$+CH), 1.68 (6H, m, 3×CH$_2$), 1.30 (9H, m, 3×CH$_3$).

A solution of 38.3 g of ethyl P-cyclohexylmethyl-P-diethoxymethylphosphinate in 27 ml of water is treated with 27 ml of 37% aqueous hydrochloric acid and the mixture heated to reflux for 5 hours. The mixture is cooled to room temperature and washed with ether/hexane 1:1. Three phases are obtained. The lower 2 phases are removed and the water is removed under reduced pressure to afford cyclohexylmethylphosphonous acid as a white solid; $^1$H-NMR (CDCl$_3$): δ (ppm)=7.40 (1H, broad singlet, exchanges D$_2$O, P—OH), 7.12 (1H, d, J=526 Hz, H—P), 2.10-1.75 (7H, m, 3×CH$_2$+CH), 1.48-1.05 (6H, m, 3×CH$_3$).

A tetrahydrofuran solution of 19.3 g of cyclohexylmethylphosphonous acid is cooled to 5°, at which temperature a suspension forms, and treated with 12.14 g of triethylamine. An exothermia ensues and the suspension is re-cooled to 5° before slow addition of 13.02 g ethyl chloroformate in 20 ml of anhydrous tetrahydrofuran. An exothermic reaction occurs with gas evolution. The white suspension is stirred overnight at room temperature and subsequently filtered. The filtrate is concentrated under reduced pressure and the residue partitioned between dichloromethane and water. The organic phase is removed, dried and concentrated in vacuo to give a yellow oil. Distillation in high vacuum affords ethyl (cyclohexylmethyl)phosphinate; b.p. 120°-130° (2×10$^{-2}$ mbar); $^1$H-NMR (CDCl$_3$): δ (ppm)=7.17 (1H, d, J=527 Hz, P—H), 4.13 (2H, m, CH$_2$OP), 1.95-1.58 (7H, m, 3×CH$_2$+CH), 1.38-0.75 (9H, m, 3×CH$_2$+CH$_3$).

A suspension of 2.25 g of sodium hydride (55% dispersion in oil) in 10 ml of anhydrous tetrahydrofuran is cooled to 0° under an inert atmosphere. A solution of 8.9 g of ethyl (cyclohexylmethyl)phosphinate in 10 ml of anhydrous tetrahydrofuran is added dropwise maintaining the temperature at between 0°-5°. After the addition is complete the suspension is warmed to room temperature and stirred for 30 minutes before re-cooling to 0° C. A solution of 19.87 g of methyl iodide in 10 ml of anhydrous tetrahydrofuran is added slowly—very exothermic! After warming to room temperature, the reaction mixture is stirred for 45 minutes, re-cooled to 0° and carefully treated with water. Removal of the organic phase, drying and concentration affords a yellow oil. Chromatography on silica gel gives ethyl P-cyclohexylmethyl-P-methylphosphinate as a colourless oil; $^1$H-NMR (CDCl$_3$): δ (ppm)=4.04 (2H, m, CH$_2$OP), 1.94-1.57 (7H, m, 3×CH$_2$+CH), 1.45 (3H, d, J=15 Hz, P—CH$_3$), 1.36-0.95 (9H, m, 3×CH$_2$+CH$_3$).

A solution of 4.14 g lithium diisopropylamide in 60 ml of anhydrous tetrahydrofuran is cooled to −73° C. under an inert atmosphere. With constant stirring a −78° solution of 7.9 g of ethyl P-cyclohexylmethyl-P-methylphosphinate in 20 ml of anhydrous tetrahydrofuran is added over 15 minutes under a positive pressure of an inert atmosphere via a canula. The resulting pale yellow solution is stirred for 1 hour at −78° and a pre-cooled (−78°) solution of 1.22 g N-tert.-butoxycarbonylglycine methyl ester in 30 ml of anhydrous tetrahydrofuran is added over 5 minutes via a canula. Chromatographic analysis after 15 minutes stirring at −78° indicates the reaction to be complete. At −78° 2.21 g glacial acetic acid is added and the mixture allowed to warm to room temperature. The reaction is diluted with dichloromethane and washed with water. Drying of the solvent and removal under reduced pressure affords a pale yellow oil.

Removal of the starting material by distillation and chromatography of the residue on silica-gel gives ethyl 3-(N-tert.-butoxycarbonylamino)-2-oxo-propyl(cyclohexylmethyl)phosphinate as a pale yellow oil; $^1$H-NMR (CDCl$_3$): δ (ppm)=5.5 (1H, br s, exch. D$_2$O, NH), 4.10 (4H, m, CH$_2$OP+CH$_2$N), 3.10 (2H, AB$_q$, d, CH$_2$C=O), 1.95-1.58 (7H, m, 3×CH$_2$+CH), 1.44 (9H, s, tBu), 1.38-0.95 (9H, m, 3×CH$_2$+CH$_3$).

EXAMPLE 5

A solution of 0.73 g of sodium 3-(N-tert.-butoxycarbonylamino)-2-hydroxy-2-methyl-propyl(n-butyl)phosphinate is dissolved in 10 ml of 1.0 aqueous hydrochloric acid and the solution stirred at 20° for 16-20 hours. After this time the solution is washed with dichloromethane followed by ether and the water removed under reduced pressure at 40° to afford an oily solid. This solid is treated with n-propanol and a few grams of charcoal. Subsequent heating to reflux and filtration gives a colourless solution. Removal of the solvent in vacuo and drying of the solid in vacuo at 80° gives a pale yellow solid. Dissolution of this solid in absolute ethanol followed by treatment with propylene oxide affords a white solid. Recrystallisation from an ethanol/acetone mixture gives 3-amino-2-hydroxy-2-methylpropyl(n-butyl)phosphinic acid of m.p. 187°-189°.

The starting materials may be obtained as follows:

A solution of 13.44 g of methallylamine hydrochloride and 27.3 g of di-tert.-butyl carbonate in 250 ml of dichloromethane at 20° is treated with 25.2 g of triethylamine. The solution is stirred for 1 hour at 20° washed with water and the organic phase is dried and the solvent is removed to give a colourless oil. Flash-chromatography on silica-gel affords pure 3-(N-tert.-butoxycarbonylamino)-2-methyl-prop-2-ene as a colourless oil; $^1$H-NMR (CDCl$_3$): δ (ppm)=4.83 (2H, m, 2×CH=C), 4.70–4.60 (1H, broad s, exch. D$_2$O, NH), 3.67 (2H, s, CH$_2$N), 1.73 (3H, s, CH$_3$), 1.45 (9H, s, tBu).

A solution of 27.18 g of m-chloroperbenzoic acid in chloroform is cooled to circa 10° under argon and treated, by dropwise addition, with a chloroform solution of 17.1 g of 3-(N-tert.-butoxycarbonylamino)-2-methyl-prop-2-ene over a period of 1 hour maintaining the temperature below 15° with external cooling. About 30 minutes after the addition is complete and a white precipitate begins to form. Completeness of the reaction can be judged by chromatographic analysis. When the reaction is complete, the suspension is diluted with chloroform and washed with 3×300 ml of a 10% aqueous solution of sodium bisulphite followed by 3×300 ml of a 10% aqueous solution of sodium bicarbonate. Drying of the organic layer and removal of the solvent in vacuo afforded 3-(N-tert.-butoxycarbonylamino)-2-methyl-2,3-epoxypropane as a colourless oil; $^1$H-NMR (CDCl$_3$): δ (ppm)=3.3 (2H, t, CH$_2$N), 2.65 (2H, AB$_q$, CH$_2$) 1.43 (9H, s, tBu), 1.33 (3H, s, CH$_3$).

A solution of 15.0 g of ethyl n-butylphosphinate in anhydrous tetrahydrofuran containing 11.11 g of triethylamine is treated under an inert gas with an anhydrous tetrahydrofuran solution of 11.95 g of trimethylchlorosilane. A white precipitate forms immediately and the resulting suspension is stirred for 24 hours at room temperature under an inert gas. The reaction mixture is then filtered under an inert gas and the filtrate concentrated in vacuo to afford a cloudy oil which is then treated with 3.76 g of 3-(N-tert.-butoxycarbonylamino)-2-methyl-2,3-epoxypropane and 1 g of anhydrous zinc chloride. An exothermic reaction results. After the exotherm has subsided the clear solution is heated slowly to 70° and stirred at this temperature for 4 hours, after which time chromatographic analysis indicates the reaction to be complete. The reaction mixture is cooled to room temperature, diluted with dichloromethane and washed with water. Drying of the solvent and removal in vacuo affords an oil. The excess starting material is removed by Kugelrohr-distillation in high vacuum and the pale yellow residue chromatographed on silica-gel to give ethyl 3-(N-tert.-butoxycarbonylamino)-2-hydroxy-2-methyl-propyl-(n-butyl)-phosphinate as a colourless oil; $^1$H-NMR (CDCl$_3$): δ (ppm)=5.17+4.68 (1H, Exch. D$_2$O, NH), 4.07 (2H, m, CH$_2$OP), 3.18 (2H, m, CH$_2$N), 1.93–1.22 (24H, m, becomes 23H on D$_2$O exchange), 0.92 (3H, t,CH$_3$). $^{31}$P-NMR (CDCl$_3$); 59.6, 59.3.

A solution of 0.86 g of ethyl 3-(N-tert.-butoxycarbonylamino)-2-hydroxy-2-methyl-propyl-(n-butyl)-phosphinate in 10 ml of ethanol is treated with a solution of 0.4 g of sodium hydroxide in 3 ml of water and the resulting solution is heated to 60° for 24 hours. After this time the reaction is cooled to 20° and the solvent removed. The residue is partitioned between dichloromethane and water and the aqueous phase is removed and concentrated in vacuo. This residue is dissolved in hot n-propanol and filtered through celite. After removal of the n-propanol sodium 3-(N-tert.-butoxycarbonylamino)-2-hydroxy-2-methyl-propyl(n-butyl)phosphinate is obtained as a pale yellow hygroscopic solid which can be used without any further purification.

EXAMPLE 6

A solution of 0.64 g of ethyl 3-(N-tert.-butoxycarbonylamino)-2-oxo-propyl(cyclopropylmethyl)phosphinate in 10 ml of anhydrous dichloromethane under an inert atmosphere at room temperature is treated with 1.53 g of trimethylbromosilane. The pale yellow solution is stirred for 4 hours at room temperature and the volatile materials are removed under reduced pressure to give a pale yellow oil. This oil is redissolved in methanol containing 1% water and the clear pale yellow solution is stirred for 30 minutes at room temperature. The solvent is removed and the residue is dried in high vacuum at 50° C. for 24 hours to afford 3-amino-2-oxo-propyl(cyclopropylmethyl)phosphinic acid hydrobromide salt as a yellow gum. This gum is dissolved in ethanol and treated with propylene oxide to afford, after filtration and drying 3-amino-2-oxo-propyl(cyclopropylmethyl)phosphinic acid as a pale yellow solid of m.p. 109°–110° C.; $^1$H-NMR (D$_2$O): δ (ppm)=4.15 (2H, s, CH$_2$N), 3.18 (2H, d, J=15 Hz, CH$_2$P), 1.58 (2H, d, d, J=15+6 Hz, PCH$_2$), 0.83 (1H, m, CH), 0.55 (2H, m, CH$_2$), 0.17 (2H, m, CH$_2$).

The starting material may be obtained as follows:

A suspension of 2.22 g of sodium hydride (80% in oil) in 50 ml of anhydrous tetrahydrofuran under an inert atmosphere at 20° is treated with 50 ml of an anhydrous tetrahydrofuran solution of 7.24 g of ethyl (methyl)-phosphinate at such a rate so that the temperature does not exceed 25°. After the addition is complete the resulting suspension is stirred for 1 hour at room temperature before slow addition of 10.0 g of bromomethylcyclopropane. The reaction mixture is stirred for a further 3 hours at 20° cooled in an ice/water bath and 100 ml of water added carefully. The clear solution is then partitioned between dichloromethane and water. Separation of the organic layer followed by drying and removal of the solvent affords a pale yellow oil. Distillation under high vacuum affords ethyl cyclopropylmethyl(methyl)-phosphinate of b.p. 100° C. (10$^{-1}$ mbar); $^1$H-NMR (CDCl$_3$): δ (ppm)=4.04 (2H, m, CH$_2$OP) 1.66 (2H, d, CH$_2$P), 1.47 (3H, d, CH$_3$), 1.30 (3H, t, CH$_3$) 0.88 (1H, m, CH), 0.55 (2H, m, CH$_2$), 0.15 (2H, m, CH$_2$).

A solution of 6.97 g of lithium diisopropylamide in 100 ml of anhydrous tetrahydrofuran is cooled to −78° under an inert atmosphere. With constant stirring, a −78° solution of 10.5 g of ethyl cyclopropylmethyl(methyl)phosphinate in 30 ml of absolute tetrahydrofuran is added over 15–20 minutes via a canula under a positive pressure of inert gas. The resulting pale yellow solution is stirred for 1 hour at −78° and a pre-cooled (−78°) solution of 2.06 g of N-tert.-butoxycarbonyl glycine methyl ester in 20 ml absolute tetrahydrofuran is added over 5–10 minutes via a canula. Chromatographic analysis after 15 minutes stirring at −78° C. indicated the reaction to be complete. At −78° 3.75 ml of glacial acetic acid is added and the mixture allowed to warm to room temperature. The reaction mixture is diluted with dichloromethane and washed with water. Drying of the solvent and removal under reduced pressure affords a pale yellow oil. Removal of the excess starting material by distillation and chromatography of the residue on silica gel gives ethyl 3-(N-tert.-butoxycarbonylamino)-2-oxo-propyl(cyclopropylmethyl)phosphinate as a pale yellow oil; $^1$H-NMR (CDCl$_3$): δ (ppm)=5.40 (1H, Br t, Exch. D$_2$O, NH), 4.14 (4H, m, CH$_2$OP+CH$_2$N) 3.17

(2H, d, J=17.5 Hz, CH₂C=O), 1.93-1.68 (2H, m, PCH₂), 1.45 (9H, s, tBu), 1.35 (3H, t, CH₃), 0.93 (1H, m, CH), 0.62 (2H, m, CH₂), 0.27 (2H, m, CH₂).

EXAMPLE 7

A solution of 0.3 g ethyl 3-(N-tert.butoxycarbonylamino)-2-(4-chlorophenyl)-2-hydroxy-propyl(n-butyl)phospinate in 5 ml of anhydrous dichloromethane is treated with 0.53 g of trimethylbromosilane and the resulting colourless solution is stirred for 24 hours at room temperature under an inert atmosphere. The volatile materials are removed under reduced pressure to give an off-white foam, which is redissolved in 5 ml of methanol containing 1% of water and the solution is stirred for 20 hours at room temperature. After this time, evaporation of the solvent in vacuo followed by drying of the resulting solid in high vacuum gives 3-amino-3-(4-chlorophenyl)-2-hydroxypropyl-n-butyl phosphinic acid hydrobromide. Dissolution of this salt in ethanol and treatment with propylene oxide gives 3-amino-2-(4-chlorophenyl)-2-hydroxy-propyl-(n-butyl)phosphinic acid of m.p. 215°-216.5°; ¹H-NMR (D₂O): δ (ppm)=7.32 (4H, m, Ph), 3.26 (2H, s, CH₂N), 2.40 (2H, m, CH₂P), 1.07 (6H, m, 3×CH₂), 0.88 (3H, t, CH₃).

The starting material may be prepared as follows:

A solution of 218 g of propa-1,2-dienylphosphinic acid in 900 ml of anhydrous dichloromethane is cooled to 10° under an inert atmosphere and treated with 167.5 g of triethylamine. A slight exothermia results, and the mixture is re-cooled to 10° before dropwise addition of 180 g of ethyl chloroformate dissolved in 200 ml of dichloromethane over 130 minutes maintaining the temperature at between 10° and 15°. Gas evolution results and a white precipitate is formed. The suspension is stirred overnight and filtered. The solid obtained is washed with tetrahydrofuran and the combined washings and filtrate are washed with water. The organic phase are combined, and dried, and the solvent is removed under reduced pressure. Distillation in high vacuum affords ethyl propa-1,2-dienyl phosphinate of b.p. 47°-50° C. (6×10⁻³ mbar); ¹H-NMR (CDCl₃): δ(ppm)=7.21 (1H, d, d, J=576+477 P—H), 5.43 (1H, t, d, d, CH), 5.10 (2H, d, CH₂), 4.14 (2H, m, CH₂OP), 1.36 (3H, t, CH₃).

A solution of 41.25 g of ethyl propa-1,2-dienyl phosphinate in 100 ml of triethyl orthoacetate is treated with 1 g of boron trifluoride diethyl etherate. After 3 hours at room temperature the solution is diluted with dichloromethane and washed with a 10% aqueous sodium bicarbonate solution. The organic phase is dried and the volatile materials are removed under reduced pressure. Distillation of the residue in high vacuum affords ethyl 1,1-diethoxyethyl-(propa-1,2-dienyl)phosphinate of b.p. 89°-125° (10⁻³ mbar) as a colourless oil. ¹H-NMR (CDCl₃): δ(ppm)=5.44 (1H, d, d, CH), 5.02 (2H, d, d, CH₂), 4.22 (2H, m, CH₂OP), 3.65 (4H, m, 2×CH₂OC), 1.53 (3H, d, J=16 Hz, P—C—CH₃), 1.33 (3H, t, CH₃), 1.20 (6H, t, 2×CH₃).

A solution of 4.78 g 4-chloroiodobenzene in 20 ml of dry diethyl ether is added to 0.486 g of magnesium turnings under argon so that the metal is just covered with the solvent. Reaction is initiated by gently warming and the remainder of the chloroiodobenzene ether solution is added at such a rate so as to maintain a gentle reflux. After the addition is complete the mixture is refluxed for a further 1 hour. The brown cloudy solution is then cooled to 0° and added slowly to a suspension of 4.1 g of copper(1)bromide dimethyl sulphide complex in dry ether pre-cooled to −45°. The resulting orange/yellow suspension is stirred at −45° for 1-1½ hours.

Then a chilled ether solution of 4.979 g of ethyl 1,1-dimethoxyethyl-(propa-1,2-dienyl)phosphinate is added over 30 minutes maintaining the temperature at less than or equal to −40°. The mustard coloured suspension is stirred for 2½ hours at −40° followed by 1½ hours at −20°. To the light red suspension a saturated ammonium chloride solution is added and warmed slowly to room temperature. The reaction mixture is partitioned between dichloromethane and water. The organic phase is dried and the solvent is removed in vacuo to give a semi-solid residue which is suspended in ether and filtered. Removal of the ether and chromatography of the residue on silica gel affords ethyl 1,1-diethoxyethyl-2-(4-chlorophenyl)-prop-1-enyl phosphinate as a pale yellow oil. ¹H-NMR (CDCl₃): δ(ppm)=7.40 (4H, m, Ph), 5.53 (1H, d, CH), 5.35 (1H, d, CH), 4.06 (2H, q, CH₂OP), 3.90-3.60 (4H, m, 2×CH₂OC), 3.06 (2H, d, J=15 Hz, P—CH₂), 1.55 (3H, d, J=15 Hz, P—CH₃), 1.30-1.05 (9H, t, 3×CH₃).

A solution of 14.42 g of ethyl 1,1-diethoxyethyl-2-(4-chlorophenyl)-prop-1-enyl phosphinate in 50 ml of anhydrous dichloromethane containing 10% absolute ethanol is treated with 6.518 g of trimethylchlorosilane. After stirring at room temperature for 24 hours the volatile material is removed under reduced pressure. Chromatography of the resulting oil on silica-gel gives ethyl 2-(4-chlorophenyl)-prop-1-enyl phosphinate as a colourless oil; ¹H-NMR (CDCl₃): δ(ppm)=7.35 (4H, m, Ph), 7.05 (1H, d, t, J=549 and 1.5 Hz, P—H), 5.56 (1H, d, CH), 5.30 (1H, d, CH), 4.20-3.97 (2H, q, CH₂OC), 3.07 (2H, d, J=1.5 Hz, P—CH₂), 1.27 (3H, t, CH₃).

A tetrahydrofuran solution of 2.5 g of ethyl 2-(4-chlorophenyl)prop-1-enylphosphinate is cooled to −78° under an inert atmosphere and one equivalent of n-butyl lithium in hexane is added over 15-20 minutes so that the internal temperature remains below −70°. The pale yellow solution is stirred for additional 15 minutes at −78° and then treated with 1.95 g of n-butyl iodide maintaining the temperature at −78°. After additional 10 minutes at −78°, the reaction is quenched with a saturated aqueous solution of ammonium chloride and warmed to 0°. Dilution with dichloromethane and washing saturated aqueous ammonium chloride solution followed by drying and removal of the solvent affords an oil. Careful chromatography on silica-gel gives ethyl (n-butyl) 2-(4-chlorophenyl)prop-1-enylphosphinate as a colourless oil; ¹H-NMR (CDCl₃): δ(ppm)=7.38 (4H, m, Ph), 5.48 (1H, d, CH), 5.32 (1H, d, CH), 4.11-3.80 (2H, m, CH₂OP), 3.02 (2H, d, J=16 Hz, CH₂P), 1.65 (2H, m, PCH₂), 1.51 (2H, m, CH₂), 1.33 (2H, m, CH₂), 1.20 (3H, t CH₃), 0.57 (3H, t, CH₃).

An absolute methanol solution of 2.34 g of tert.-butyl carbamate is cooled to 0° under an inert atmosphere and treated carefully with 2.17 g of tert.-butyl hypochlorite. The resulting pale yellow solution is stirred for 15 minutes at 0° and a solution of 0.84 g of sodium hydroxide in 10 ml of absolute methanol added dropwise. The cooling bath is removed and the solution stirred for 10 minutes before removal of the methanol. Trituration of the remaining slurry with ether and collection of the solid by filtration followed by drying in high vacuo affords sodium N-chloro-tert.-butylcarbamate.

An acetonitrile suspension of 0.69 g sodium N-chloro-tert.-butylcarbamate is treated with 0.675 g of silver nitrate and the resulting brown suspension treated with 0.6 g of ethyl (n-butyl) 2-(4-chlorophenyl)prop-1-enylphosphinate followed by 10.18 mg of osmium tetroxide and 180 g of water. The black suspension is stirred at room temperature for 24 hours and filtered through celite. The filtrate is treated with 20 ml of 5% aqueous sodium sulphite and the two phase mixture heated to reflux for 2 hours. After cooling to room temperature the acetonitrile is removed in vacuo and the aqueous layer extracted with chloroform. Drying of the organic layer and removal of the solvent affords an oil. Chromatography on silica gel gives ethyl 3-N-(tert.-butyloxycarbonyl) amino-2-(4-chlorophenyl)-2-hydroxy-propyl (n-butyl)phosphinate as a white waxy solid, m.p. 85°–90°; (diastereomeric mixture). $^1$H-NMR (CDCl$_3$): $\delta$(ppm) = 7.39 (Ph) 6.05–5.90 (exch D$_2$O, OH), 5.09 (exch D$_2$O, NH), 4.17–3.95 (CH$_2$OP+CHN), 4.67–4.44 (CHOP+CHN), 4.25–4.07 (CH$_2$N), 2.40–2.12 (CH$_2$P), 1.73–1.0 (tBu, 3×CH$_3$+CH$_3$), 0.89 (CH$_3$), 0.75 (CH$_3$).

EXAMPLE 8

Analogously to the method described in Example 7 3-amino-2-(4-chlorophenyl)2-hydroxy-propyl(methyl)-phosphinic acid of m.p. 219°–220° can be obtained; $^1$H-NMR (D$_2$O): $\delta$(ppm) = 7.43 (4H, m, Ph), 3.36 (2H, AB$_2$, CH$_2$N), 2.66–2.35 (2H, m, CH$_2$P), 1.09 (3H, d, J = 14.54 Hz P—Me).

EXAMPLE 9.

In an analogous manner as described in Example 3, 3-amino-1,1-difluoro-propyl(n-butyl)phosphinic acid and its hydrochloride can be obtained starting from ethyl butylphosphinate by deprotonation with sodium hydride and reaction with bromodifluoromethane in tetrahydrofuran at 0° followed by reaction with n-butyllithium in tetrahydrofuran under an Argon atmosphere at −70° and subsequently with N-(p-nitrobenzoyl)aziridine and treatment of the resulting ethyl 3-(p-nitrobenzoylamino)-1,1-difluoro-propyl(n-butyl)phosphinate with boiling hydrochloric acid.

EXAMPLE 10

A solution of 0.48 g of ethyl 3-(N-tert.-butoxycarbonylamino)-2-(4-chlorophenyl)-2-hydroxy-propyl(diethoxymethyl)phosphinate in 10 ml of anhydrous dichloromethane is treated with 0.76 g of trimethylbromosilane and the resulting colourless solution stirred for 24 hours at room temperature under an inert atmosphere. The volatile materials are removed under reduced pressure to give a foam which is redisslued in 5 ml of methanol containing 1% of water and the solution stirred for 20 hours at room temperature. After this time evaporation of the solvent in vacuo followed by chromatography of the residue on reverse-phase silicagel and drying of the off white solid thus obtained in high vacuum gives 3-amino-2-(4-chlorophenyl)-2-hydroxypropyl(-diethoxymethyl)phosphinic acid hydrobromide salt. Dissolution of the salt in the methanol and treatment with propylene oxide gives 3-amino-2-(4-chlorophenyl)-2-hydroxy-propyl(diethoxymethyl)phosphinic acid; $^1$H-NMR (D$_2$O): $\delta$(ppm) = 7.39 (4H, m, Ph), 4.75 (1H, d, CH—P), 3.67–3.23 (6H, m, 2×CH$_2$CO+CH$_2$N), 2.38–1.97 (2H, AB$_q$, CH$_2$P), 1.23–1.04 (6H, t, 2×CH$_3$).

The starting material may be obtained as follows:

A solution of 218 g of propa-1,2-dienyl phosphinic acid in 900 ml of anhydrous dichloromethane is cooled to 10° under an inert atmosphere and treated with 167.5 g of triethylamine. A slight exotherm results and the mixture is re-cooled to 10° before dropwise addition of 180 ml of a dichloromethane solution of 180 g ethyl chloroformate over 130 minutes maintaining the temperature at between 10° and 15°, gas evolution results and a white precipitate is formed. The suspension is stirred overnight and filtered. The solid is washed with carbon tetrachloride and the combined washings and filtrate washed with water. The organic phase is dried and the solvent removed under reduced pressure. Distillation in high vacuum affords ethyl propa-1,2-dienyl phosphinate of b.p. 47°–50° (6×10$^{-3}$ mbar); $^1$H-NMR (CDCl$_3$): $\delta$(ppm) = 7.21 (1H, d, d, J = 576+4 Hz, P—H), 5.43 (1H, t, d, d, CH), 5.10 (2H, d, CH$_2$), 4.14 (2H, m, CH$_2$OC), 1.36 (3H, t, CH$_3$).

A solution of 41.25 g of ethyl propa-1,2-dienyl phosphinate in 100 ml of triethyl orthoacetate is treated with 1 g of boron trifluoride diethyl etherate. After 3 hours at room temperature the solution is diluted with dichloromethane and washed with 10% aqueous sodium bicarbonate solution. The organic phase is dried and the volatile material removed under reduced pressure. Distillation of the residue in high vacuum affords ethyl (1,1-diethoxyethyl)propa-1,2-dienyl phosphinate of b.p. 80°–125° (10$^{-3}$ mbar) as a colourless oil. $^1$H-NMR (CDCl$_3$): $\delta$(ppm) = 5.44 (1H, d, d, CH), 5.02 (2H, d, d, CH$_2$) 4.22 (2H, m, CH$_2$OP), 3.65 (4H, m, 2×CH$_2$OC), 1.53 (3H, d, J = 16 Hz, P—CH$_2$), 1.33 (3H, t, CH$_3$), 1.20 (6H, t, 2×CH$_3$), 130–1.05 (9H, t, 3×CH$_3$).

A solution of 4.78 g 4-chloroiodobenzene in 20 ml of dry diethyl ether is added to 0.486 g of magnesium turnings under argon so that the metal is just covered with the solvent. Reaction is initiated by gently warming and the remainder of the chloroiodobenzene ether solution is added at such a rate so as to maintain a gentle reflux. After the addition is complete the mixture is refluxed for a further 1 hour. The brown cloudy solution is then cooled to 0° and added slowly to a suspension of 4.1 g of copper(1)bromide dimethyl sulphide complex in dry ether pre-cooled to −45°. The resulting orange/yellow suspension is stirred at −45° for 1–1½ hours before addition of a chilled ether solution of 4.97 g of ethyl (1,1-diethoxyethyl)propa-1,2-dienyl phosphinate over 30 minutes maintaining the temperature at less than as equal to −40°. The mustard coloured suspension is stirred for 2½ hours at −40° followed by 1½ hours at −20°. To the light red suspension is added saturated ammonium chloride solution and warmed slowly to room temperature. The reaction is partitioned between dichloromethane and water. The organic phase is dried and the solvent removed in vacuo to give a semi-solid residue which is suspended in ether and filtered. Removal of the ether and chromatography of the residue on silicagel affords ethyl 2-(4-chlorophenyl)(1,1-diethoxyethyl)prop-1-enyl phosphinate as a pale yellow oil. $^1$H-NMR (CDCl$_3$): $\delta$(ppm) = 7.40 (4H, m, PH), 5.53 (1H, d, CH) 5.35 (1H, d, CH), 4.06 (2H, q, CH$_2$OP), 3.90–3.60 (4H, m, 2×CH$_2$OC), 3.06 (2H, d, J = 15 Hz, P—CH$_2$), 1.55 (3H, d, J = 15 Hz, P—CH$_3$).

A solution of 14.42 g of ethyl (1,1-diethoxyethyl)-2-(4-chlorophenyl)prop-1-enylphosphinate in 50 ml of anhydrous dichloromethane containing 10% of absolute ethanol is treated with 6.518 g of trimethylchlorosilane. After stirring at room temperature for 24 hours the volatile material is removed under reduced pressure. Chromatography of the resulting oil on silica-gel gives ethyl 2-(4-chlorophenyl)prop-1-enylphosphinate as a colourless oil; $^1$H-NMR (CDCl$_3$): δ(ppm)=7.35 (4H, m, Ph), 7.05 (1H, d, t, J=549 and 1.5 Hz, P—H), 5.56 (1H, d, CH), 5.30 (1H, d, CH), 4.20–3.97 (2H, q, CH$_2$OP), 3.07 (2H, d, t, J=17+1.5 Hz, P—CH$_2$), 1.27 (3H, t, CH$_3$).

A solution of 1.68 g of ethyl 2-(4-chlorophenyl)prop-1-enylphosphinate in 20 ml of triethyl orthoformate is treated with 0.1 g of boron trifluoride diethyl etherate and the resulting solution stirred for 7 days at room temperature. The reaction mixture is then treated with 20 ml 10% aqueous sodium hydrogen carbonate solution and extracted twice with dichloromethane. The organic layer is removed, dried and concentrated to give an oil. Chromatography on silica gel gives ethyl 2-(4-chlorophenyl)prop-1-enyl-(diethoxymethyl)phosphinate as a colourless oil. $^1$H-NMR (CDCl$_3$): δ(ppm)=7.38 (4H, m; Ph), 5.51 (1H, d, CH), 4.62 (1H, d, CH—P), 4.05 (2H, q, CH$_2$OP), 3.88–3.56 (CH, m, 2×CH$_2$OC), 2.07 (2H, d, d, CH$_2$P), 1.28–1.14 (9H, m, 3×CH$_3$).

Reaction of ethyl 2-(4-chlorophenyl)prop-1-enyl(diethoxymethyl)phosphinate with tertiary butyl N-chloro-N-iodo-carbamate in the presence of osmium tetroxide in an analogous manner as described in Example 7 gives ethyl 3-(N-tert.-butoxycarbonylamino)-2-(4-chlorophenyl)-2-hydroxy-propyl(diethoxymethyl)p hosphinate as a colourless oil; $^1$H-NMR (CDCl$_3$): δ(ppm)=7.46-7.26 (4H, m, Ph), 5.66 +5.22 (1H, exchange with D$_2$O, OH), 5.07·(1H, exchange with D$_2$O, NH), 4.52 (1H, d, CH—P), 4.18 (2H, m, CH$_2$OP, diastereomer A), 3.9–3.05 (8H, m, 2×CH$_2$OC, CH$_2$N, CH$_2$OP), 2.59–2.20 (2H, AB$_q$, CH$_2$P), 1.37 (9H, s, tert.-butyl), 1.33–0.90 (9H, m, 3×CH$_3$).

EXAMPLE 11

In a manner analogous to the method described in Example 7, 3-amino-2-(4-chlorophenyl)-2-hydroxy-propyl(cyclohexylmethyl)phosphinic acid can be manufactured.

EXAMPLE 12

In a manner analogous to the method described in Example 7, 3-amino-2-(4-chlorophenyl)-2-hydroxy-propyl(benzyl)phosphinic acid can be manufactured.

EXAMPLE 13

In a manner analogous to the method described in Example 7, 3-amino-2-(4-chlorophenyl)-2-hydroxy-propyl(cyclopropylmethyl)phosphinic acid can be manufactured.

EXAMPLE 14

In a manner analogous to the method described in Example 6, 3-amino-2-(4-chlorophenyl)-2-oxo-propyl(benzyl)phosphinic acid can be manufactured.

EXAMPLE 15

In a manner analogous to the method described in Example 6, 3-amino-2-(4-chlorophenyl)-2-oxo-propyl(diethoxymethyl)phosphinic acid can be manufactured.

EXAMPLE 16

Preparation of 10,000 tablets each containing 100 mg of the active ingredient, for example, 3-amino-2-oxo-propyl(n-butyl)phosphinic acid, can be manufactured as follows:

| Composition | |
|---|---|
| Active ingredient | 1,000.00 g |
| Lactose | 257.00 g |
| Corn starch | 75.00 g |
| Polyethylene glycol 6,000 | 75.00 g |
| Magnesium stearate | 18.00 g |
| Purified water | q.s |

Procedure: All the powders are passed through a screen with openings of 0.6 mm. Then the drug substance, lactose, magnesium stearate and half of the starch are mixed in a suitable mixer. The other half of the starch is suspended in 40 ml of water and the suspension added to the boiling solution of the polyethylene glycol in 150 ml of water. The paste formed is added to the powders which are granulated, if necessary, with an additional amount of water. The granulate is dried overnight at 35°, broken on a screen with 1,2 mm openings and compressed into tablets with 12.8 mm diameter, uppers bisected.

EXAMPLE 17

Preparation of 10,000 capsules each containing 25 mg of the active ingredient, for example, 3-amino-2-oxo-propyl(n-butyl)phosphinic acid, can be manufactured as follows:

| Composition | |
|---|---|
| Active ingredient | 250.0 g |
| Lactose | 1,750.0 g |

Procedure: All the powders are passed through a screen with openings of 0.6 mm. Then the drug substance is placed in a suitable mixer and mixed with the lactose until homogeneous. No. 3 capsules are filled with 200 mg using a capsule filling machine.

EXAMPLE 18

In a manner analogous to that described in Examples 16 and 17 tablets and capsules comprising as the active ingredients 10–100 mg of another compounds of the invention, e.g. as described in the Examples 1 to 15.

We claim:

1. A compound of the formula I

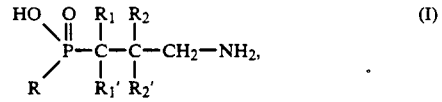

wherein either: R$_1$ is halogen, R$_1$' is halogen or hydrogen and R$_2$ and R$_2$' denote hydrogen or; R$_1$ and R$_1$' represent hydrogen, R$_2$ is an aliphatic or aromatic radical and R$_2$' is hydroxy or; R$_2$ and R$_2$' together represent oxo, and wherein R denotes an aliphatic, cycloaliphatic, cycloaliphatic-aliphatic or araliphatic radical having 2 or more carbon atoms or; if R$_1$ and R$_1$' denote hydrogen, R$_2$ represents an aromatic radical and R$_2$' is hydroxy, R represents methyl, or a salt thereof.

2. A compound as claimed in claim 1, of the formula I, wherein R$_1$ is halogen, R$_1$' is halogen or hydrogen and R$_2$ and R$_2$' are hydrogen or R$_1$ and R$_1$' are hydrogen, R$_2$ denotes lower alkyl, phenyl, phenyl mono- or disubstituted by halogen, lower alkyl, lower alkoxy and/or trifluoromethyl or pyridyl and R$_2$' is hydroxy or R$_2$ and $R_2'$ together represent oxo, and wherein R denotes lower alkyl having 2 or more carbon atoms, lower alkenyl, lower alkynyl, a cycloalkyl, hydroxycycloalkyl, cycloalkyl-lower alkyl, cycloalkyl-(hydroxy)lower alkyl or lower alkylthiocycloalkyl-(hydroxy)-lower alkyl group having 3 to 6 ring carbon atoms, oxo-lower alkyl, amino-lower alkyl, lower alkanoylamino-lower alkyl, phthalimido-lower alkyl, mono- or dihydroxy-lower alkyl, hydroxy-lower alkenyl, amino-(hydroxy)-lower alkyl, lower alkanoylamino-(hydroxy)lower alkyl, phthalimido-(hydroxy)lower alkyl, mono-, di- or polyhalogeno-lower alkyl, mono-, di- or polyhalogeno-lower alkenyl, mono-, di- or polyhalogeno-(hydroxy)-lower alkyl, mono-, di- or polyhalogeno-(hydroxy)-lower alkenyl, amino lower alkoxy-lower alkyl, lower alkylthio-lower alkyl, lower alkanesulphinyl-lower alkyl, lower alkanesulphonyl-lower alkyl, di-lower alkoxy-lower alkyl, di-lower alkylthio-lower alkyl, lower alkoxy-(hydroxy)lower alkyl, lower alkoxy-(halogeno)-lower alkyl, phenyl-lower alkyl, phenyl-lower alkyl mono- or disubstituted, in the phenyl moiety, by halogen, lower alkyl, lower alkoxy and/or trifluoromethyl, naphthyl-lower alkyl, oxa- or thiacycloalkyl having 2 to 6 ring carbon atoms, or dioxa-, oxathia- or dithiacycloalkyl having 3 to 5 ring carbon atoms or, if $R_1$ and $R_1'$ denote hydrogen, $R_2$ represents phenyl, phenyl mono- or disubstituted by halogen, lower alkyl, lower alkoxy and/or trifluoromethyl or pyridyl and $R_2'$ is hydroxy, R represents methyl, or a salt thereof.

3. A compound as claimed in claim 1, of the formula I, wherein $R_1$ is halogen, $R_1'$ is halogen or hydrogen and $R_2$ and $R_2'$ are hydrogen or $R_1$ and $R_1'$ are hydrogen, $R_2$ denotes phenyl or phenyl mono- or disubstituted by halogen, lower alkyl, lower alkoxy and/or trifluoromethyl and $R_2'$ is hydroxy or $R_2$ and $R_2'$ together represent oxo, and wherein R denotes lower alkyl having 2 or more carbon atoms, lower alkenyl, lower alkynyl, a cycloalkyl, hydroxycycloalkyl, cycloalkyl-lower alkyl, cycloalkyl-(hydroxy)lower alkyl or lower alkylthiocycloalkyl-(hydroxy)-lower alkyl group having 3 to 6 ring carbon atoms, oxo-lower alkyl, amino-lower alkyl, lower alkanoylamino-lower alkyl, phthalimido-lower alkyl, mono- or dihydroxy-lower alkyl, hydroxy-lower alkenyl, amino-(hydroxy)lower alkyl, lower alkanoylamino-(hydroxy)lower alkyl, phthalimido-(hydroxy)lower alkyl, mono-, di- or polyhalogeno-lower alkyl, mono-, di- or polyhalogeno-lower alkenyl, mono-, di- or polyhalogeno-(hydroxy)lower alkyl, mono-, di- or polyhalogeno-(hydroxy)lower alkenyl, amino lower alkoxy-lower alkyl, lower alkylthio-lower alkyl, lower alkanesulphinyl-lower alkyl, lower alkanesulphonyl-lower alkyl, di-lower alkoxy-lower alkyl, di-lower alkylthio-lower alkyl, lower alkoxy-(hydroxy)lower alkyl, lower alkoxy-(halogeno)lower alkyl, phenyl-lower alkyl, phenyl-lower alkyl mono- or disubstituted, in the phenyl moiety, by halogen, lower alkyl, lower alkoxy and/or trifluoromethyl, naphthyl-lower alkyl, oxa- or thiacycloalkyl having 2 to 6 ring carbon atoms, or dioxa-, oxathia- or dithiacycloalkyl having 3 to 5 ring carbon atoms, or a salt thereof.

4. A compound as claimed in claim 1, of the formula I, wherein either $R_1$ and $R_1'$ are fluoro and $R_2$ and $R_2'$ represent hydrogen or $R_1$ and $R_1'$ are hydrogen, $R_2$ is phenyl, phenyl substituted by halogen, $C_1$–$C_4$alkyl, $C_1$–$C_4$alkoxy and/or trifluoromethyl and $R_2'$ is hydroxy or $R_1$ and $R_1'$ are hydrogen and $R_2$ and $R_2'$ together represent oxo, and wherein R is $C_2$–$C_{12}$-alkyl, $C_2$–$C_7$-alkenyl, $C_2$–$C_7$-alkynyl, mono- or dihydroxy-$C_2$–$C_7$-alkyl, oxo-$C_3$–$C_7$alkyl, amino-$C_3$–$C_6$alkyl, phthalimido-$C_3$–$C_6$alkyl or phthalimido-$C_3$–$C_7$(hydroxy)alkyl, or a salt thereof.

5. A compound as claimed in claim 1, of the formula I, wherein $R_1$ and $R_1'$ are fluoro and $R_2$ and $R_2'$ are hydrogen, or $R_1$ and $R_1'$ are hydrogen and $R_2$ and $R_2'$ together represent oxo, and wherein R denotes $C_2$–$C_7$-alkyl, α-saturated $C_3$–$C_7$-alkenyl, α-saturated $C_3$–$C_7$-alkynyl, α-, β-, γ- or δ-hydroxy-$C_2$–$C_7$-alkyl, α,α-difluoro-$C_2$–$C_4$-alkyl, mono-, di-or trifluoro-α-hydroxy-$C_3$–$C_7$-alkyl, mono-, di- or trihalogeno-α-hydroxy-$C_3$–$C_7$-alkenyl, $C_1$–$C_4$-alkoxy-$C_1$–$C_4$-alkyl, di-$C_1$–$C_4$-alkoxy-$C_1$–$C_4$-alkyl, $C_3$–$C_6$-cycloalkyl-$C_1$–$C_4$-alkyl, α-hydroxy-$C_3$–$C_6$-cycloalkyl or $C_3$–$C_6$-cycloalkyl-α-hydroxy-$C_1$–$C_4$-alkyl, or a salt thereof.

6. A compound as claimed in claim 1, of the formula I, wherein $R_1$ and $R_1'$ are hydrogen, $R_2$ is phenyl, phenyl substituted by halogen, $C_1$–$C_4$alkyl, $C_1$–$C_4$alkoxy and/or trifluoromethyl and $R_2'$ is hydroxy, and wherein R represents $C_1$–$C_7$alkyl, or a salt thereof.

7. A compound as claimed in claim 1, wherein R is $C_2$–$C_7$-alkyl, and wherein $R_1$ and $R_1'$ are fluoro and $R_2$ and $R_2'$ are hydrogen, or $R_1$ and $R_1'$ are hydrogen and $R_2$ and $R_2'$ together represent oxo, or a salt thereof.

8. A compound as claimed in claim 1 being 3-amino-2-(4-chlorophenyl)-2-hydroxypropyl(n-butyl)phosphinic acid or a salt thereof.

9. A compound as claimed in claim 1 being 3-amino-1,1-difluoro-propyl(n-butyl)phosphinic acid or a salt thereof.

10. A compound as claimed in claim 1 being 3-amino-2-oxo-propyl(cyclopropylmethyl)phosphinic acid or a salt thereof.

11. A compound as claimed in claim 1 being 3-amino-2-oxo-propyl(cyclohexylmethyl)phosphinic acid or a salt thereof.

12. A compound as claimed in claim 1 being 3-amino-2-hydroxy-2-methyl-propyl(n-butyl)phosphinic acid or a salt thereof.

13. A compound as claimed in claim 1 being 3-amino-1-fluoro-propyl(n-butyl)phosphinic acid or a salt thereof.

14. A compound as claimed in claim 1 being 3-amino-2-(4-chlorphenyl)-2-hydroxypropyl(cyclohexylmethyl)phosphinic acid or a salt thereof.

15. A compound as claimed in claim 1 being 3-amino-2-(4-chlorophenyl)-2-hydroxypropyl(benzyl)phosphinic acid or a salt thereof.

16. A compound as claimed in claim 1 being 3-amino-2-(4-chlorophenyl)-2-hydroxypropyl(cyclopropylmethyl)phosphinic acid or a salt thereof.

17. A compound as claimed in claim 1 being 3-amino-2-(4-chlorophenyl)-2-hydroxypropyl(cyclopropylmethyl)phosphinic acid or a salt thereof.

18. A compound as claimed in claim 1 being 3-amino-2-(4-chlorophenyl)-2-oxo-propyl(diethoxymethyl)phosphinic acid or a salt thereof.

19. A compound as claimed in claim 1 being 3-amino-2-(4-chlorophenyl)-2-hydroxy-propyl(diethoxymethyl)phosphinic acid or a salt thereof.

20. A compound as claimed in claim 1 being 3-amino-2-(4-chlorophenyl)-2-hydroxypropyl(methyl)phosphinic acid or a salt thereof.

21. A pharmaceutical composition which contains at least one compound as claimed in claim 1 in admixture to conventional pharmaceutical excipients.

22. A method for the treatment of cerebral insufficiencies, depressions and/or anxieties, characterized in that a therapeutically effective amount of a compound claimed in claim 1 is administered to a warm-blooded organism in need of such treatment.

* * * * *